United States Patent
Fallin et al.

(10) Patent No.: US 10,682,131 B2
(45) Date of Patent: Jun. 16, 2020

(54) INTRA JOINT STABILIZATION CONSTRUCT

(71) Applicant: Mortise Medical, LLC, Logan, UT (US)

(72) Inventors: T. Wade Fallin, Hyde Park, UT (US); Justin Taber, Honolulu, HI (US); Matthew Karam, North Liberty, IA (US); Phinit Phisitkul, Coralville, IA (US)

(73) Assignee: CROSSROADS EXTREMITY SYSTEMS, LLC, Memphis, TN (US)

( * ) Notice: Subject to any disclaimer, the term of this patent is extended or adjusted under 35 U.S.C. 154(b) by 239 days.

(21) Appl. No.: 15/641,573

(22) Filed: Jul. 5, 2017

(65) Prior Publication Data

US 2018/0008255 A1 Jan. 11, 2018

Related U.S. Application Data

(60) Provisional application No. 62/358,231, filed on Jul. 5, 2016, provisional application No. 62/425,560, filed
(Continued)

(51) Int. Cl.
*A61B 17/04* (2006.01)
*A61B 17/06* (2006.01)
(Continued)

(52) U.S. Cl.
CPC ...... *A61B 17/0401* (2013.01); *A61B 17/0485* (2013.01); *A61B 17/06166* (2013.01);
(Continued)

(58) Field of Classification Search
CPC . A61B 17/864; A61B 17/8625; A61B 17/842; A61B 17/0401; A61B 17/0487; A61F 2002/0882; A61F 2002/0888
See application file for complete search history.

(56) References Cited

U.S. PATENT DOCUMENTS 2,181,746 A 11/1939 Siebrandt
2,291,413 A 7/1942 Siebrandt
(Continued)

FOREIGN PATENT DOCUMENTS

CA 551446 A 1/1958
EP 132284 A1 1/1985
(Continued)

OTHER PUBLICATIONS

International Search Report and Written Opinion for Int. Appl. No. PCT/US2017/064173 dated Feb. 14, 2018, 8 pp.
(Continued)

*Primary Examiner* — Thomas McEvoy
(74) *Attorney, Agent, or Firm* — David Meibos; Maywood IP Law

(57) ABSTRACT

The disclosure provides devices and methods of use pertaining to intra joint stabilization. Embodiments include a number of suture returning and suture locking anchors that feature elongated sleeves configured to protect the associated bone tunnels from suture wipering, which results in abrasion and enlargement of the bone tunnel and leads to migration of the suture anchors. Embodiments also include suture locking anchors that lock via an interference fit between the suture strand and a receiver of the anchor and a set screw, where the receiver and the set screw each feature a number of gradual, opposing tapers to facilitate gradual proximal-to-distal gripping and releasing of the suture strand to achieve an optimal locking force while preventing severing of the suture strand. Further embodiments include intra joint reinforcement and stabilization constructs formed using the disclosed devices. Other embodiments are disclosed.

13 Claims, 31 Drawing Sheets

Related U.S. Application Data on Nov. 22, 2016, provisional application No. 62/456,217, filed on Feb. 8, 2017, provisional application No. 62/458,975, filed on Feb. 14, 2017.

(51) Int. Cl.
  *A61B 17/16* (2006.01)
  *A61B 90/00* (2016.01)
  *A61B 17/88* (2006.01)
  A61B 17/80 (2006.01)
  A61B 17/00 (2006.01)
  A61B 17/84 (2006.01)

(52) U.S. Cl.
  CPC ........ *A61B 17/1604* (2013.01); *A61B 17/885* (2013.01); *A61B 17/8869* (2013.01); *A61B 90/06* (2016.02); A61B 17/80 (2013.01); A61B 17/848 (2013.01); A61B 2017/00526 (2013.01); A61B 2017/00867 (2013.01); A61B 2017/0403 (2013.01); A61B 2017/0404 (2013.01); A61B 2017/044 (2013.01); A61B 2017/045 (2013.01); A61B 2017/0409 (2013.01); A61B 2017/0414 (2013.01); A61B 2017/0441 (2013.01); A61B 2017/0445 (2013.01); A61B 2017/0453 (2013.01); A61B 2017/0464 (2013.01); A61B 2090/061 (2016.02)

(56) References Cited

U.S. PATENT DOCUMENTS

| | | |
|---|---|---|
| 2,362,957 A | 11/1944 | Hackett |
| 2,427,128 A | 9/1947 | Ettinger |
| 2,485,531 A | 10/1949 | William |
| 2,489,870 A | 11/1949 | William |
| 2,511,051 A | 6/1950 | William |
| 2,706,475 A | 4/1955 | Reynolds |
| 2,715,403 A | 8/1955 | Jordan |
| 3,114,367 A | 12/1963 | Carpenter |
| 3,664,022 A | 5/1972 | Small |
| 3,727,611 A | 4/1973 | Schultz |
| 3,867,932 A | 2/1975 | Huene |
| 3,959,960 A | 6/1976 | Santos |
| 4,050,464 A | 9/1977 | Hall |
| 4,159,716 A | 7/1979 | Borchers |
| 4,364,381 A | 12/1982 | Sher |
| D273,326 S | 4/1984 | Peterson |
| 4,586,497 A | 5/1986 | Dapra |
| 4,587,963 A | 5/1986 | Leibinger |
| 4,712,542 A | 12/1987 | Daniel |
| 4,787,377 A | 11/1988 | Laboureau |
| 4,945,904 A | 8/1990 | Bolton |
| 4,964,862 A | 10/1990 | Arms |
| 4,969,471 A | 11/1990 | Daniel |
| 4,969,895 A | 11/1990 | McLeod |
| 5,035,701 A | 7/1991 | Kabbara |
| 5,116,340 A | 5/1992 | Songer |
| 5,300,077 A | 4/1994 | Howell |
| 5,306,290 A | 4/1994 | Martins |
| 5,312,410 A | 5/1994 | Miller |
| 5,312,412 A | 5/1994 | Whipple |
| 5,409,490 A | 4/1995 | Ethridge |
| 5,431,659 A | 7/1995 | Ross, Jr. |
| 5,449,361 A | 9/1995 | Preissman |
| 5,476,465 A | 12/1995 | Preissman |
| 5,540,698 A | 7/1996 | Preissman |
| 5,545,168 A | 8/1996 | Burke |
| 5,570,706 A | 11/1996 | Howell |
| 5,578,057 A | 11/1996 | Wenstrom, Jr. |
| 5,584,839 A | 12/1996 | Gieringer |
| 5,643,321 A | 1/1997 | McDevitt |
| 5,713,897 A | 2/1998 | Goble |
| 5,725,532 A | 3/1998 | Shoemaker |
| 5,741,281 A | 4/1998 | Martin |
| 5,868,748 A | 2/1999 | Burke |
| 5,895,389 A | 4/1999 | Schenk |
| 6,001,106 A | 12/1999 | Ryan |
| 6,027,523 A | 2/2000 | Schmieding |
| 6,045,573 A | 4/2000 | Wenstrom |
| 6,254,604 B1 | 7/2001 | Howell |
| 6,254,605 B1 | 7/2001 | Howell |
| 6,368,326 B1 | 4/2002 | Dakin |
| 6,443,955 B1 | 9/2002 | Ahrend |
| 6,478,753 B2 | 11/2002 | Reay |
| 6,482,208 B1 | 11/2002 | Ahrend |
| 6,517,564 B1 | 2/2003 | Grafton |
| 6,527,794 B1 | 3/2003 | McDevitt |
| 6,547,778 B1 | 4/2003 | Sklar |
| 6,554,852 B1 | 4/2003 | Oberlander |
| 6,557,426 B2 | 5/2003 | Reinemann, Jr. |
| 6,616,667 B1 | 9/2003 | Steiger |
| 6,660,023 B2 | 12/2003 | McDevitt |
| 6,669,698 B1 | 12/2003 | Tromanhauser |
| 6,739,068 B1 | 5/2004 | Rinner |
| 6,761,722 B2 | 7/2004 | Cole |
| 6,780,198 B1 | 8/2004 | Gregoire |
| 6,866,673 B2 | 3/2005 | Oren |
| 7,060,068 B2 | 6/2006 | Tromanhauser |
| 7,081,126 B2 | 7/2006 | McDevitt |
| 7,083,638 B2 | 8/2006 | Foerster |
| 7,090,690 B2 | 8/2006 | Foerster |
| 7,160,285 B2 | 1/2007 | Sklar |
| 7,172,626 B1 | 2/2007 | Andrews |
| 7,211,088 B2 | 5/2007 | Grafton |
| 7,226,469 B2 | 6/2007 | Benavitz |
| 7,235,091 B2 | 6/2007 | Thornes |
| 7,326,222 B2 | 2/2008 | Dreyfuss |
| 7,431,692 B2 | 10/2008 | Zollinger |
| 7,442,202 B2 | 10/2008 | Dreyfuss |
| 7,455,683 B2 | 11/2008 | Geissler |
| 7,537,596 B2 | 5/2009 | Jensen |
| 7,556,630 B2 | 7/2009 | Molz |
| 7,572,275 B2 | 8/2009 | Fallin |
| 7,578,824 B2 | 8/2009 | Justin |
| 7,637,926 B2 | 12/2009 | Foerster |
| 7,871,368 B2 | 1/2011 | Zollinger |
| 7,875,058 B2 | 1/2011 | Holmes, Jr. |
| 7,887,551 B2 | 2/2011 | Bojarski |
| 7,901,431 B2 | 3/2011 | Shurnas |
| 7,963,966 B2 | 6/2011 | Cole |
| 7,998,149 B2 | 8/2011 | Hamilton |
| 8,083,769 B2 | 12/2011 | Cauldwell |
| 8,109,936 B2 | 2/2012 | Tipirneni |
| 8,114,127 B2 | 2/2012 | West |
| 8,114,128 B2 | 2/2012 | Cauldwell |
| 8,162,997 B2 | 4/2012 | Struhl |
| 8,167,906 B2 | 5/2012 | Cauldwell |
| 8,182,495 B2 | 5/2012 | DiStefano |
| 8,221,455 B2 | 7/2012 | Shurnas |
| 8,277,459 B2 | 10/2012 | Sand |
| 8,277,484 B2 | 10/2012 | Barbieri |
| 8,298,247 B2 | 10/2012 | Sterrett |
| 8,303,591 B1 | 11/2012 | Foerster |
| 8,317,828 B2 | 11/2012 | Martinek |
| 8,343,186 B2 | 1/2013 | Dreyfuss |
| 8,394,123 B2 | 3/2013 | Cauldwell |
| 8,414,599 B1 | 4/2013 | Foerster |
| 8,460,379 B2 | 6/2013 | Albertorio |
| 8,500,745 B2 | 8/2013 | Kuenzi |
| 8,506,597 B2 | 8/2013 | Kaiser |
| 8,579,901 B1 | 11/2013 | Foerster |
| 8,597,328 B2 | 12/2013 | Cauldwell |
| 8,613,755 B1 | 12/2013 | Foerster |
| 8,617,185 B2 | 12/2013 | Bonutti |
| 8,623,049 B2 | 1/2014 | Ward |
| 8,623,051 B2 | 1/2014 | Bojarski |
| 8,623,052 B2 | 1/2014 | Dreyfuss |
| 8,679,122 B2 | 3/2014 | Bernstein |
| 8,696,719 B2 | 4/2014 | Lofthouse |
| 8,715,297 B1 | 5/2014 | Foerster |
| 8,764,763 B2 | 7/2014 | Foerster |
| 8,764,797 B2 | 7/2014 | Dreyfuss |

(56) References Cited

U.S. PATENT DOCUMENTS

| | | |
|---|---|---|
| 8,790,344 B1 | 7/2014 | Foerster |
| 8,795,286 B2 | 8/2014 | Sand |
| 8,801,755 B2 | 8/2014 | Dreyfuss |
| 8,814,902 B2 | 8/2014 | Bonutti |
| 8,821,541 B2 | 9/2014 | Dreyfuss |
| 8,870,876 B2 | 10/2014 | Lettmann |
| 8,876,900 B2 | 11/2014 | Guederian |
| 8,882,833 B2 | 11/2014 | Saylor |
| 8,888,815 B2 | 11/2014 | Holmes, Jr. |
| 8,926,626 B2 | 1/2015 | Mannava |
| 8,939,999 B2 | 1/2015 | Sterrett |
| 8,945,026 B2 | 2/2015 | Moser |
| 8,961,575 B2 | 2/2015 | Choinski |
| 8,979,850 B2 | 3/2015 | Johnstone |
| 8,984,720 B2 | 3/2015 | Gephart |
| 9,017,330 B2 | 4/2015 | Foerster |
| 9,039,682 B2 | 5/2015 | Lampropoulos et al. |
| 9,072,509 B2 | 7/2015 | Stoll, Jr. |
| 9,107,701 B2 | 8/2015 | Cole |
| 9,131,937 B2 | 9/2015 | Chan |
| 9,138,219 B2 | 9/2015 | Horrell |
| 9,161,748 B2 | 10/2015 | West |
| 9,179,907 B2 | 11/2015 | ElAttrache |
| 9,179,950 B2 | 11/2015 | Zajac |
| 9,186,133 B2 | 11/2015 | Gregoire |
| 9,204,872 B2 | 12/2015 | Loepke |
| 9,259,217 B2 | 2/2016 | Fritzinger |
| 9,271,715 B2 | 3/2016 | Cauldwell |
| 9,277,912 B2 | 3/2016 | Donate |
| 9,521,999 B2 | 12/2016 | Dreyfuss |
| 9,526,493 B2 | 12/2016 | Dreyfuss |
| 9,532,776 B2 | 1/2017 | Lo |
| 9,549,726 B2 | 1/2017 | Dreyfuss |
| 9,622,739 B2 | 4/2017 | Dreyfuss |
| 2001/0049483 A1 | 12/2001 | Reay |
| 2002/0087190 A1 | 7/2002 | Benavitz |
| 2002/0188297 A1 | 12/2002 | Dakin |
| 2003/0009171 A1 | 1/2003 | Tornier |
| 2003/0176920 A1 | 9/2003 | Sklar |
| 2004/0098045 A1 | 5/2004 | Grafton |
| 2004/0102788 A1 | 5/2004 | Huebner |
| 2004/0153153 A1 | 8/2004 | Elson |
| 2005/0065533 A1 | 3/2005 | Magen |
| 2005/0070906 A1 | 3/2005 | Clark |
| 2005/0222618 A1 | 10/2005 | Dreyfuss |
| 2005/0240226 A1 | 10/2005 | Foerster |
| 2006/0085006 A1 | 4/2006 | Ek |
| 2006/0161159 A1 | 7/2006 | Dreyfuss |
| 2006/0271060 A1 | 11/2006 | Gordon |
| 2006/0276804 A1 | 12/2006 | Molz |
| 2006/0293709 A1 | 12/2006 | Bojarski |
| 2007/0060922 A1 | 3/2007 | Dreyfuss |
| 2007/0060931 A1 | 3/2007 | Hamilton |
| 2007/0073299 A1 | 3/2007 | Dreyfuss |
| 2007/0083236 A1 | 4/2007 | Sikora |
| 2007/0088362 A1 | 4/2007 | Bonutti |
| 2007/0150003 A1 | 6/2007 | Dreyfuss |
| 2007/0198036 A1 | 8/2007 | Sklar |
| 2007/0225764 A1 | 9/2007 | Benavitz |
| 2007/0288027 A1 | 12/2007 | Grafton |
| 2008/0077182 A1 | 3/2008 | Geissler |
| 2009/0043153 A1 | 2/2009 | Zollinger |
| 2009/0228049 A1 | 9/2009 | Park |
| 2009/0306711 A1 | 12/2009 | Stone et al. |
| 2010/0010496 A1 | 1/2010 | Isaza |
| 2010/0160963 A1 | 6/2010 | Fallin |
| 2010/0191284 A1 | 7/2010 | Dreyfuss |
| 2010/0262185 A1* | 10/2010 | Gelfand .......... A61B 17/0401 606/232 |
| 2011/0022054 A1 | 1/2011 | DiStefano |
| 2011/0112576 A1 | 5/2011 | Nguyen |
| 2011/0184426 A1 | 7/2011 | Garces Martin |
| 2011/0224727 A1 | 9/2011 | Housman |
| 2012/0053626 A1 | 3/2012 | Koepke |
| 2012/0065677 A1 | 3/2012 | West |
| 2012/0123417 A1 | 5/2012 | Smith |
| 2012/0123428 A1 | 5/2012 | Berberich |
| 2012/0165867 A1 | 6/2012 | Denham et al. |
| 2012/0172936 A1 | 7/2012 | Horrell |
| 2012/0253410 A1 | 10/2012 | Taylor |
| 2013/0023930 A1 | 1/2013 | Stone et al. |
| 2013/0138150 A1 | 5/2013 | Baker |
| 2013/0165972 A1 | 6/2013 | Sullivan |
| 2013/0184708 A1 | 7/2013 | Robinson |
| 2013/0296937 A1 | 11/2013 | Dreyfuss |
| 2013/0345750 A1 | 12/2013 | Sullivan |
| 2014/0018828 A1 | 1/2014 | Foerster |
| 2014/0031882 A1 | 1/2014 | Schmuck |
| 2014/0039551 A1 | 2/2014 | Donahue |
| 2014/0074163 A1 | 3/2014 | West |
| 2014/0081322 A1 | 3/2014 | Sengun |
| 2014/0081323 A1 | 3/2014 | Hawkins |
| 2014/0081324 A1 | 3/2014 | Sengun |
| 2014/0081325 A1 | 3/2014 | Sengun |
| 2014/0114353 A1 | 4/2014 | Bojarski |
| 2014/0121701 A1 | 5/2014 | Dreyfuss |
| 2014/0128915 A1 | 5/2014 | Dreyfuss |
| 2014/0194907 A1 | 7/2014 | Bonutti |
| 2014/0194927 A1 | 7/2014 | Kaiser |
| 2014/0277134 A1 | 9/2014 | ElAttrache |
| 2014/0364905 A1 | 12/2014 | Lunn |
| 2014/0364909 A1 | 12/2014 | Dreyfuss |
| 2014/0371749 A1 | 12/2014 | Foerster |
| 2014/0379028 A1 | 12/2014 | Lo |
| 2015/0005779 A1 | 1/2015 | Tepic |
| 2015/0005819 A1 | 1/2015 | Dreyfuss |
| 2015/0012015 A1 | 1/2015 | Berelsman |
| 2015/0039029 A1 | 2/2015 | Wade |
| 2015/0051601 A1 | 2/2015 | Larsen |
| 2015/0073475 A1 | 3/2015 | Schaller |
| 2015/0073477 A1 | 3/2015 | Holmes, Jr. |
| 2015/0173739 A1 | 6/2015 | Rodriguez et al. |
| 2015/0201923 A1 | 7/2015 | Fan |
| 2015/0216576 A1 | 8/2015 | Foerster |
| 2015/0272567 A1 | 10/2015 | Feezor |
| 2015/0305737 A1 | 10/2015 | Conley |
| 2015/0313640 A1 | 11/2015 | O'Daly |
| 2015/0342594 A1 | 12/2015 | Stone |
| 2015/0342596 A1 | 12/2015 | Dreyfuss |
| 2015/0342651 A1 | 12/2015 | Cole |
| 2015/0351741 A1 | 12/2015 | Hawkins |
| 2016/0008041 A1 | 1/2016 | Makhlouf |
| 2016/0038201 A1 | 2/2016 | Cummings |
| 2016/0038267 A1 | 2/2016 | Allen |
| 2016/0051250 A1 | 2/2016 | Thornes |
| 2016/0051251 A1 | 2/2016 | Koepke |
| 2016/0066901 A1 | 3/2016 | Gregoire |
| 2016/0089131 A1 | 3/2016 | Wade |
| 2016/0192924 A1 | 7/2016 | Cauldwell |
| 2016/0235399 A1 | 8/2016 | Housman |
| 2016/0270902 A1 | 9/2016 | Snedeker et al. |
| 2016/0287302 A1 | 10/2016 | Horrell |
| 2016/0374661 A1 | 12/2016 | Housman et al. |
| 2017/0071592 A1 | 3/2017 | Feezor et al. |

FOREIGN PATENT DOCUMENTS

| | | |
|---|---|---|
| ES | 2226791 T3 | 4/2005 |
| JP | 2002102236 A | 4/2002 |
| WO | 2011153417 A1 | 12/2011 |
| WO | 2012092027 A2 | 7/2012 |

OTHER PUBLICATIONS

International Search Report and Written Opinion for Int. Appl. No. PCT/US2017/064178 dated Mar. 9, 2018, 9 pp.

Akros Fibulink, Akros Medical, 2017, www.akrosmedical.com, 3 pp.

Deltoid Ligament Reconstruction Tunnel Sites, Arthrex, Inc., www.arthrex.com, 2014, 2 pp.

InternalBrace—Ligament Augmentaion Repair—Deltoid Ligament, Arthex, Inc., www.arthrex.com, 2015, 2 pp.

(56) References Cited

OTHER PUBLICATIONS

InternalBrace—Advanced Treatment for Ligament & Tendon Repair, Arthrex, Inc., www.arthrex.com, 2 pp.
InternalBrace—Ligament Augmentation Repair, Arthrex, Inc., www.arthrex.com, 2015, 2 pp.
Modified Brostrom-Gould Technique for Lateral Ankle Ligament Reconstruction—Surgical Technique, Arthrex, Inc., www.arthrex.com, 2015, 6 pp.
Knotless TightRope Syndesmosis Fixation—Surgical Technique, Arthrex, Inc., www.arthrex.com, 2015, 5 pp.
Get your athlete back in the game!—Syndesmosis TightRope, Arthrex, Inc., http://cptr.it/TRHAS, 2015, 1 pp.
ZipTight Fixation System, BioMet Sports Medicine, www.biometsportsmedicine.com, 2009, 8 pp.
Nelson, Owen A., "Examination and Repair of the AITFL in Transmalleolar Fractures", J. Orthop Trauma, vol. 20, No. 9, Oct. 2006, p. 637-643.
Invisiknot—Foot and Ankle Technique Guide—Ankle Syndesmosis Repair, Operative Technique, Smith & Nephew, Inc., www.smith-nephew.com, Jun. 2017, 8 pp.
Invisiknot—Ankle Syndesmosis Repair Kit, Smith & Nephew, Inc., www.smith-nephew.com, 1 pp.
Van Heest, Tyler J., et al., "Injureis to the Ankle Syndesmosis", J. Bone Joint Surg. Am. 2014;96:603-13, http://dx.dor.org/10.2106/JBJS.M.00094, 11 pp.

\* cited by examiner

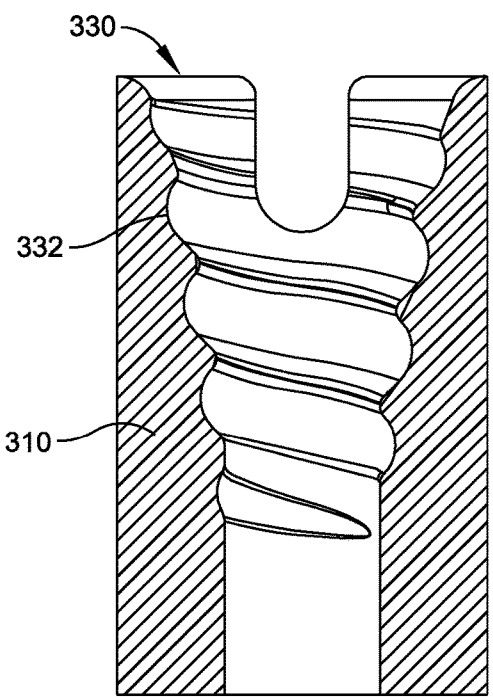 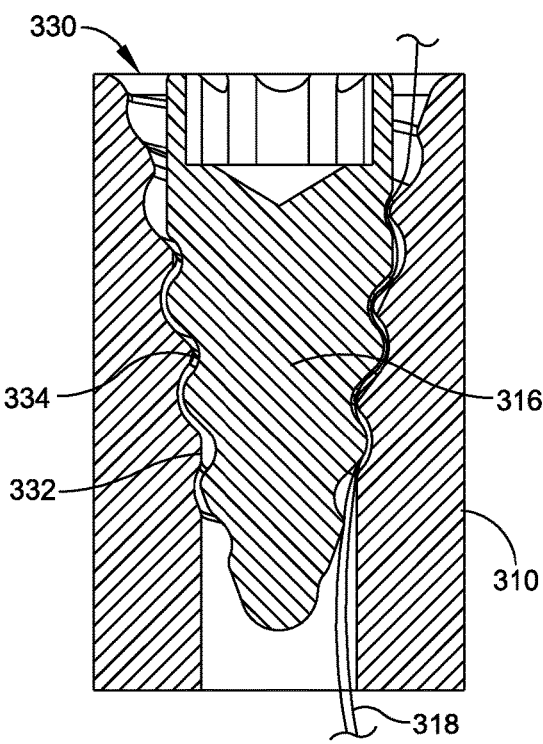
FIG. 20　　　　　　　FIG. 21
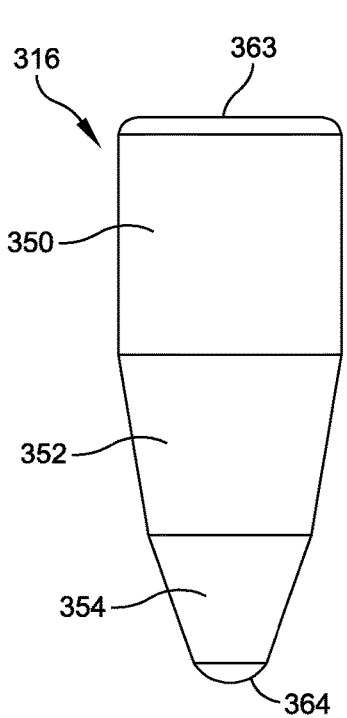 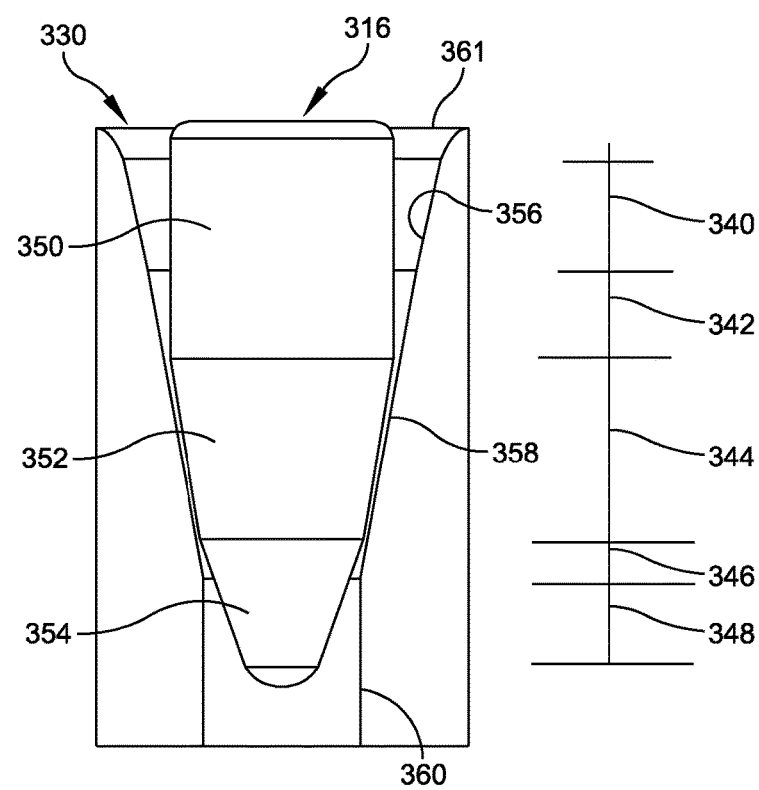
FIG. 22　　　　　　　FIG. 23

INTRA JOINT STABILIZATION CONSTRUCT

REFERENCE TO PENDING PRIOR PATENT APPLICATIONS

This application claims the benefit under 35 U.S.C. 119(e) of U.S. Provisional Patent Application Nos. 62/358,231, filed Jul. 5, 2016 by Justin Taber and T. Wade Fallin for "LIGAMENT REINFORCEMENT DEVICES AND METHODS," 62/425,560 filed Nov. 22, 2016 by Justin Tabor, Phinit Phisitkul, and T. Wade Fallin for "LIGAMENT REINFORCEMENT DEVICES AND METHODS," 62/456,217, filed Feb. 8, 2017 by Justin Taber and T. Wade Fallin for "PLATE AND LOOP CONSTRUCT," and 62/458,975, filed Feb. 14, 2017 by Matthew Karam, Phinit Phisitkul, Justin Taber, and T. Wade Fallin for "PELVIC FRACTURE REPAIR," all of which patent applications are hereby incorporated herein by reference.

REFERENCE TO CO-FILED APPLICATIONS

This application was co-filed with the following U.S. patent application numbers on Jul. 5, 2017: 15/641,592, by Justin Taber and T. Wade Fallin for "EXTRA JOINT STABILIZATION CONSTRUCT,"; 15/641,600 by Justin Taber and T. Wade Fallin for "NONCIRCULAR BROACH AND METHODS OF USE,"; 15/641,618 by Phinit Phisitkul, Justin Taber, and T. Wade Fallin for "MULTIPLE SUTURE THREADER AND METHOD OF USE,"; and 15/642,053 by Justin Taber and T. Wade Fallin for "COMPRESSION AND TENSION INSTRUMENTS AND METHODS OF USE TO REINFORCE LIGAMENTS,"; all of which patent applications are incorporated herein by reference.

BACKGROUND

Ligaments interconnect bones of the skeletal system and are involved with the stabilization and kinematics of skeletal joints. Various injuries may occur that result in compromised ligament function. Such injuries include, for example, partial and complete tears and avulsion of the bone where a ligament attaches to a bone. Ligament injuries occur throughout the skeletal system.

By way of example, the human ankle 100 is a complex junction of multiple bones and soft tissues as shown in FIGS. 1-3. The ankle includes joints between the tibia 102, fibula 104, and talus 106. The joint between the tibia 102 and fibula 104 is a syndesmosis or slightly movable joint in which the bones are joined together by connective tissue. The syndesmosis between the tibia and fibula includes the anterior inferior tibiofibular ligament (AITFL) 110, the posterior inferior tibiofibular ligament (PITFL) 112, and the interosseous ligament (IOL) 114 (FIG. 3). The syndesmosis ligaments are often injured in high ankle sprains. Other injury prone ligaments of the ankle joint include, among others, the anterior talofibular ligament (ATFL) 120, the posterior talofibular ligament (PTFL) 122 and the deltoid ligament complex 124 including superficial and deep deltoid ligaments. Current implants, instruments, and methods used to reinforce ligaments to promote healing and normal joint function present a number of challenges, and improvements are needed.

SUMMARY

This Summary is provided to introduce a selection of concepts in a simplified form that are further described below in the Detailed Description. This Summary is not intended to identify key aspects or essential aspects of the claimed subject matter. Moreover, this Summary is not intended for use as an aid in determining the scope of the claimed subject matter.

One embodiment provides an anchor for use in forming a flexible synthetic strand construct within a bone tunnel bored through a first bone portion, the bone tunnel having a first end adjacent to a first surface of the first bone portion and a second end near a second surface of the first bone portion. The anchor includes: (1) a head having a proximal side and a distal side, the distal side configured to abut the first surface of first the bone portion about the first end of the bone tunnel; (2) a longitudinal shank protruding distally from the head from a proximal end attached to the head to a distal end, the longitudinal shank defining a longitudinal axis and configured for insertion into the bone tunnel from the first end of the bone tunnel toward the second end of the bone tunnel, wherein: (a) an axial hole extends into the anchor along the longitudinal axis; (b) a length of the shank approximates a length of the bone tunnel; and (c) when, in passing from or to a separate strand fixation, a flexible synthetic strand enters or exits the axial hole at the distal end of the shank, the shank provides a bone tunnel protection sleeve that prevents transverse movement of the flexible synthetic strand relative to the bone tunnel, thereby preventing bone abrasion within the bone tunnel.

Another embodiment provides a knotless locking system for locking a flexible synthetic strand relative to a bone tunnel bored through a first bone portion, the bone tunnel having a first end adjacent to a first surface of the first bone portion and a second end near a second surface of the first bone portion. The locking system comprises a locking anchor and a set screw. The locking anchor includes: (1) a head; (2) a longitudinal shank protruding distally from the head, the shank having a proximal portion, a distal portion, and an axial hole extending therethrough, the shank defining a longitudinal axis and configured for insertion into the bone tunnel from the first end of the bone tunnel toward the second end of the bone tunnel; and (3) a receiver formed in the proximal portion of the shank, the receiver having internal threads extending over a proximal portion oriented at a proximal taper angle, a mid portion oriented at a mid taper angle, and a distal portion oriented at a distal taper angle. The set screw includes external threads extending over a proximal portion oriented at an opposing proximal taper angle, a mid portion oriented at an opposing mid taper angle, and a distal portion oriented at an opposing distal taper angle, wherein the proximal, the mid, and the distal taper angles of the receiver and the opposing proximal, the opposing mid, and the opposing distal taper angles of the set screw are configured such that when the set screw is rotationally inserted into the receiver, the set screw and the receiver provide a gradual increase in a proximal compression force applied to a length of the flexible synthetic strand extending between the proximal and the mid portions of the receiver and the set screw and a gradual decrease in a distal compression force applied to a length of the flexible synthetic strand extending between the mid and the distal portions of the receiver and the set screw.

Yet another embodiment provides an internal construct for stabilizing a joint between a first bone portion having a first bone tunnel that defines a longitudinal axis and a second bone portion having a second bone tunnel centered about the longitudinal axis. The internal construct comprises a flexible synthetic strand having first and second opposing ends tensioned between a first fixation within the first bone tunnel and a second fixation within the second bone tunnel, the first fixation comprising a locking anchor and a threaded set screw. The locking anchor includes (1) a head having a proximal side and a distal side, the distal side abutting a first surface of the first bone portion about a first end of the first bone tunnel; (2) a longitudinal shank protruding distally from the head, the shank having a proximal portion, a distal portion, and an axial hole extending therethrough, the shank inserted into the first bone tunnel from the first end of the first bone tunnel toward a second end of the first bone tunnel adjacent to the joint, the shank having a length that approximates a length of the first bone tunnel such that when the shank is inserted into the first bone tunnel, the distal portion of the shank extends to the second end of the first bone tunnel adjacent to the second surface of the first bone portion such that the shank provides a bone tunnel protection sleeve.

Additional objects, advantages and novel features of the technology will be set forth in part in the description which follows, and in part will become more apparent to those skilled in the art upon examination of the following, or may be learned from practice of the technology.

BRIEF DESCRIPTION OF THE DRAWINGS

Non-limiting and non-exhaustive embodiments of the present invention, including the preferred embodiment, are described with reference to the following figures, wherein like reference numerals refer to like parts throughout the various views unless otherwise specified. Illustrative embodiments of the invention are illustrated in the drawings, in which:

FIG. 20 illustrates a cross-sectional view of a receiver of a suture locking feature of the suture locking anchor of FIGS. 13-19;
FIG. 21 illustrates a cross-sectional view of the receiver of FIG. 20 having a set screw inserted therein to form an interference fit between a suture strand and the receiver and the set screw;
FIG. 22 illustrates a front view of the set screw of FIG. 21 without threading;
FIG. 23 illustrates the cross-sectional view of the set screw and the receiver of FIG. 21, without threading.

DETAILED DESCRIPTION

Embodiments are described more fully below in sufficient detail to enable those skilled in the art to practice the system and method. However, embodiments may be implemented in many different forms and should not be construed as being limited to the embodiments set forth herein. The following detailed description is, therefore, not to be taken in a limiting sense.

The technology discussed herein relates to apparatus and corresponding methods of use for preparing ligament reinforcement and bone fracture repair constructs. Embodiments include a number of suture returning anchors, suture locking anchors, anchor locking drivers, bone protection sleeves, and intra joint ligament reinforcement and/or bone fracture repair constructs constructed via operative methods using the devices and instruments described herein.

The disclosed devices and/or constructs may be used in conjunction with and/or employ a flexible synthetic strand such as, for example, a suture, a suture tape, a cable, or another suitable flexible synthetic strand (hereinafter a "flexible strand," "flexible synthetic strand," or "suture").

Suture Returning Anchors

Figure 4:
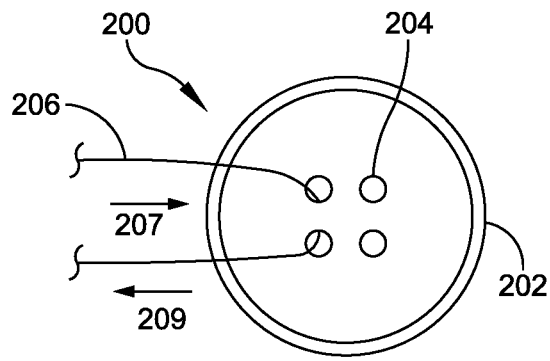
FIG. 4 illustrates a top view of one embodiment of button-like suture returning anchor.
Figure 5:
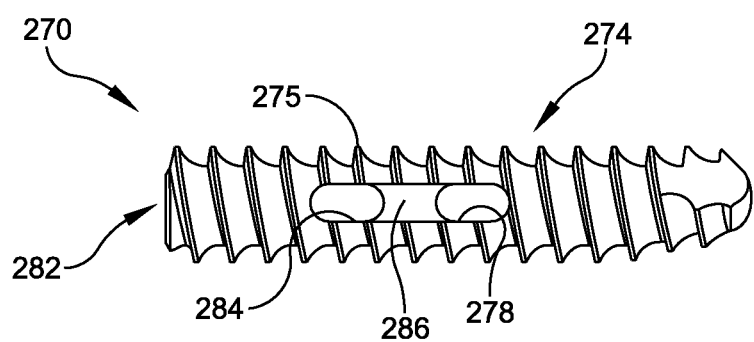
FIG. 5 illustrates a side view of one embodiment of headless screw suture returning anchor.
Figure 6:
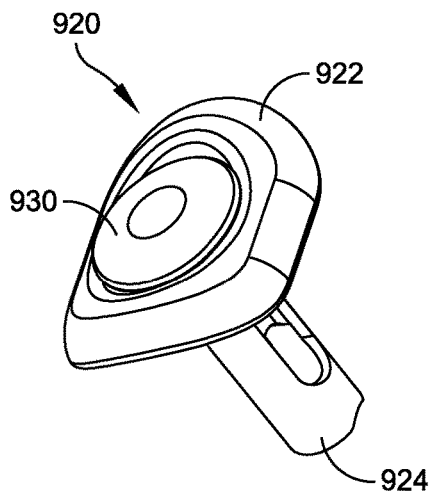
FIGS. 6-12 illustrate various perspective, front, side, rear, and cross-sectional views of one embodiment of a polyaxial suture returning anchor.
Figure 7:
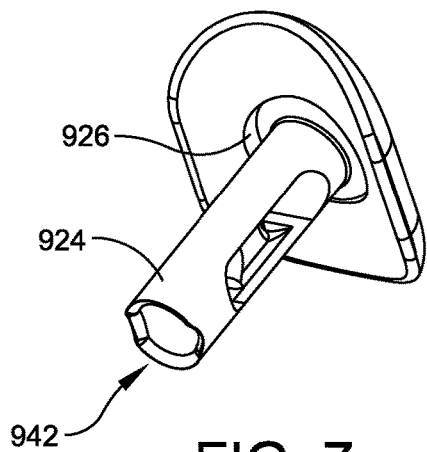
Figure 8:
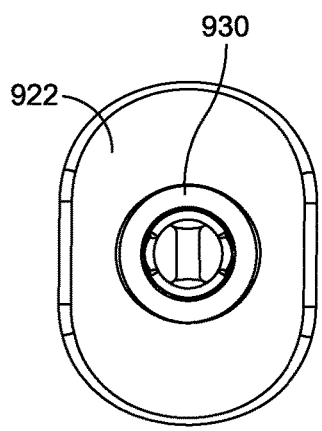
Figure 9:
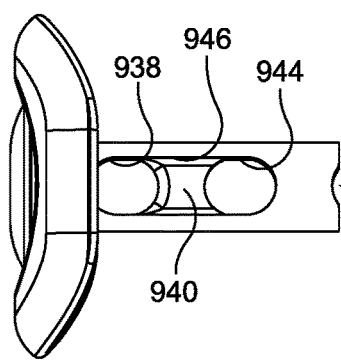
Figure 10:
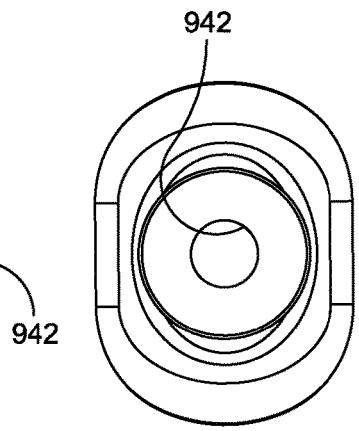
Figure 11:
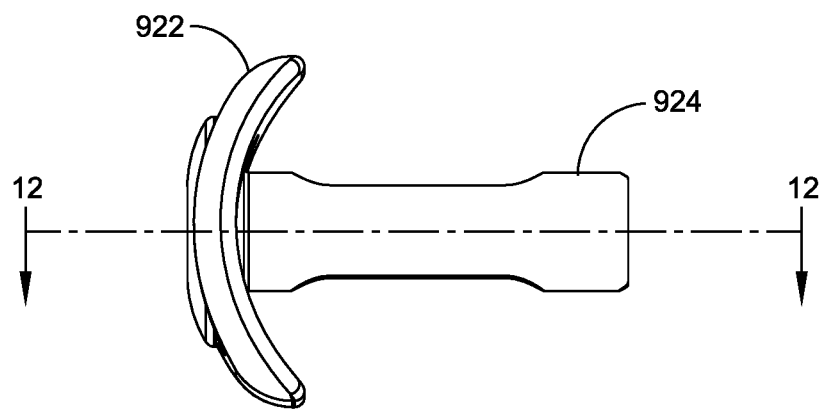
Figure 12:
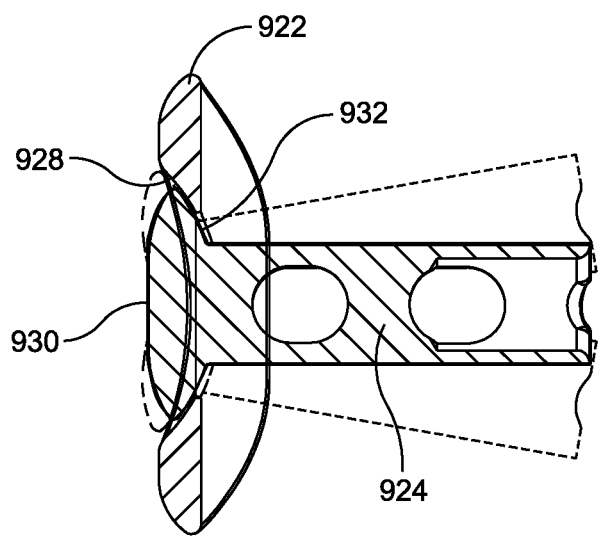
Figure 13:
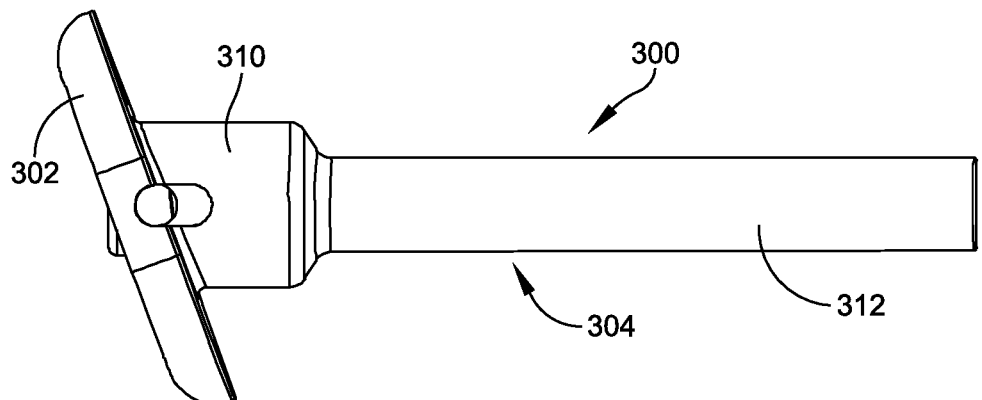
FIGS. 13-19 illustrate various perspective, front, side, rear, and cross-sectional views of one embodiment of a suture locking anchor.
Figure 14:
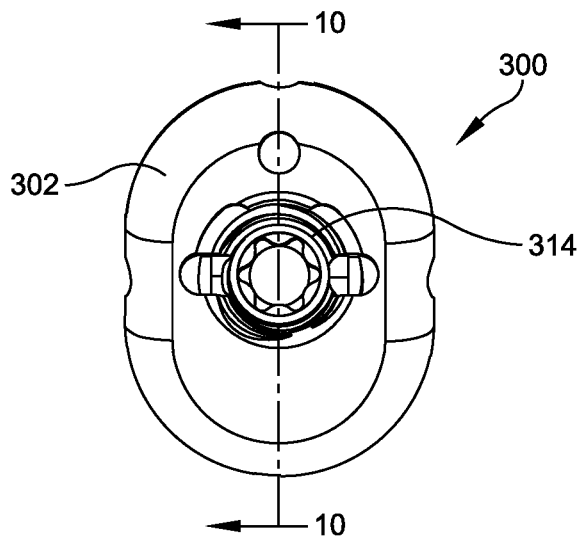
Figure 15:
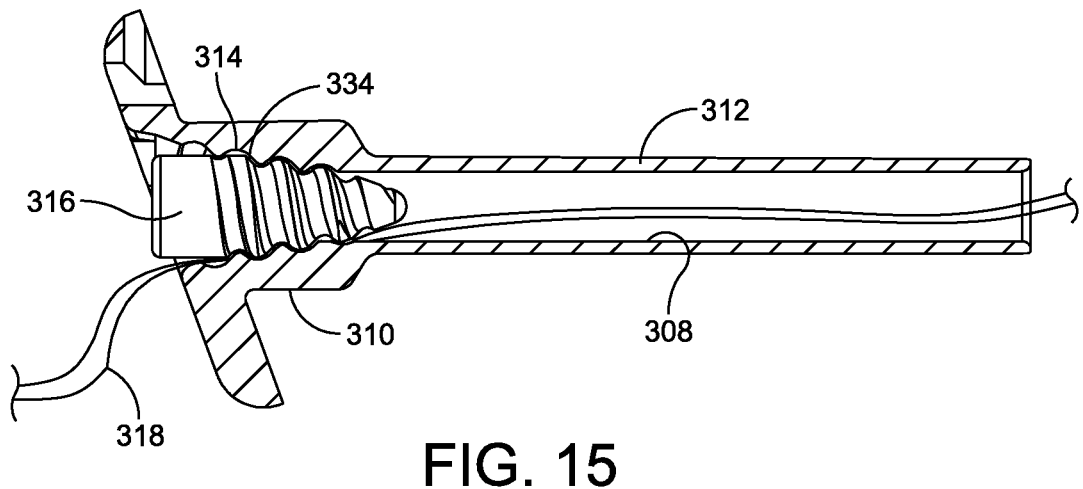

FIGS. 4-5 illustrate examples of suture returning anchors. In FIG. 4, a suture returning anchor 200 has a generally planar disc shaped body 202 in the form of a button with multiple holes 204 through the body 202. Suture 206 may be threaded through the holes 204 to secure the button to the suture. The suture 206 may be passed through a hole or tunnel in a bone such that the anchor 200 may then abut the surface of the bone adjacent the hole to prevent the suture from pulling through the hole. The anchor 200 is an example of a suture returning anchor because suture 206 may be threaded through one of the holes 204 in the anchor body in a first direction depicted by arrow 207 and then returned through another one of the holes 204 in a second, opposite direction depicted by arrow 209 such that ends of the suture 206 are provided together extending away from the anchor 200 on a common side of the anchor 200.

A suture returning anchor may be used, for example, when a suture from another portion of a reinforcement procedure needs to be anchored and tensioned using an approach from one side of the bone. The suture may have a first end fixed to another fixation structure and a second free end. The second end may be threaded through a suture returning anchor and returned so that pulling on the second end tensions the reinforcement construct. A suture returning anchor may also be used to supply two ends or a loop of suture that will be tensioned without sliding through the implant.

FIG. 5 illustrates another embodiment of a suture returning anchor 270 in the form of a headless screw that includes a shank 274 having an external spiral screw thread 275. The shank 274 includes a distal first transverse hole 278, an axial hole 282 opening at a proximal end of the shank 274, a second transverse hole 284, and relief grooves 286. A suture may be threaded into the axial hole 282 from the proximal end, out one of the openings of the second transverse hole 284, through the first transverse hole 278, in the other one of the openings of the second transverse hole 284, and out the axial hole 282 so that the suture is routed within the proximal portion of the shank. The relief grooves 286 may connect the openings of the first and the second transverse holes 278, 284 on each side of the shank 274. The relief grooves 286 allow a suture to pass from the axial hole 282 to the first transverse hole 278 while projecting less, or not at all, from an outer wall of the shank 274 to protect the suture from abrasion and to allow the suture to slide more easily while it is being routed and tensioned. A driver may be received in the axial hole 282 for driving the screw into a bone.

FIGS. 6-12 illustrate an example of a polyaxial suture returning anchor 920. In this embodiment, the anchor 920 is a two-piece anchor having a separate washer 922 and shank 924. The shank 924 extends from a proximal end at the washer 922 to a distal end spaced from the washer 922 and includes one or more transverse holes through which a suture, or flexible synthetic strand, may be threaded. In this embodiment, the shank 924 includes a first transverse hole 938 forming opposed openings on opposite sides of the shank 924 through which a suture may be threaded to provide a suture return. While the washer 922 abuts a bone, a suture may be pulled against a distal margin 940 of the hole to allow the suture to be tensioned. The shank further includes an axial hole 942 extending from an opening at its distal end toward its proximal end. A second transverse hole 944 extends through the shank 924 to form opposed openings on opposite sides of the shank 924 and which is offset distally from the first transverse hole. The second transverse hole 944 communicates with the axial hole 942.

A suture may be threaded into the axial hole 942 from the distal end, out one of the openings of the second transverse hole 944, through the first transverse hole 938, in the other of the openings of the second transverse hole 944, and out the axial hole 942 so that the suture is routed within the distal portion of the shank 924. The anchor shank 924 may further contain relief grooves 946 connecting the openings of the first and second transverse holes 938, 944 on each side of the shank 924. The relief grooves allow the suture to pass from the axial hole 942 to the first transverse hole 938 while projecting less, or not at all, from the shank sides to protect the suture from abrasion and to allow the suture to slide more easily while it is being routed and tensioned.

In the example of FIGS. 6-12 the washer 922 includes a hole 926 formed through it and a spherical seat 928 formed adjacent the hole 926. The shank 924 has a head 930 with a spherical seat 932 on its undersurface, adjacent the shank. The spherical seats 928 and 932 engage and permit the washer 922 to assume a range of angles relative to the shank 924 so that when the shank 924 is inserted into a tunnel in a bone and advanced so that the washer 922 is abutting the bone surface, the washer can angulate to match the angle between the bone tunnel and the bone surface. The adjustable polyaxial relationship between the shank 924 and the washer 922 permits the washer 922 to lie close to the bone in a low-profile manner.

Suture Locking Anchors

FIGS. 13-30 illustrate examples of suture locking anchors. FIGS. 13-19 illustrate a number of views of a suture locking anchor 300, which has a button-like head 302 and a stepped cylindrical shank 304 projecting outwardly from a distal side of the head 302 and defining a longitudinal axis 306. An axial hole 308 extends through the anchor 300. A proximal portion 310 of the shank has a larger diameter than a distal portion 312 of the shank 304. The proximal portion 310 includes internal threads 314 configured to receive external threads 334 of a set screw 316 to lock a suture within the axial hole 308.

In use, one or more sutures 318 or other flexible synthetic strands may be threaded through the axial hole 308, tensioned, and then locked in place by inserting the set screw 316 to create an interference engagement between the suture 318, the threads 334 of the set screw 316, and the threads 314 of the proximal portion 310 of the shank 304.

In the example of FIGS. 13-19, the head 302 is mounted at a non-perpendicular angle relative to the shank 304 to accommodate a suture path through a bone that is at a non-perpendicular angle to a surface of the bone against which the head 302 abuts. In this embodiment, the head 302 further includes supplemental suture holes 320, 322, 324 extending through the head 302 proximally-to-distally to allow additional sutures to be threaded through the head 302. Relief grooves 321, 323, 325 are provided on the distal surface of the head 302 and in communication with the supplemental suture holes 320, 322, 324 to provide relief for the additional sutures between the head 302 and the underlying bone.

In the example of FIGS. 13-19, the head 302 is generally oval shaped and presents a smooth surface to overlying soft tissues to reduce irritation of soft tissues. The shank 304 provides a tubular extension into a bone tunnel to protect the suture from abrasion from the bone as well as to protect the bone tunnel from abrasion or cutting from the suture.

Traditional button-style locking anchors sit on an exterior of the bone at an end of the bone tunnel and are locked via a suture knot that is tied off at the surface of the button, positioning the knot in a manner that irritates the surrounding soft tissues. Over time, the suture erodes the bone at the bone tunnel exit, and the button tends to sink or subside into the bone. Physicians have recorded up to 10 mm of migration of the button into the bone. As the bone degrades and the suture loosens, the button also develops a level of back-and-forth translational movement at the surface of the bone, which irritates both the bone and the surrounding tissues.

Embodiments of the suture locking anchor 300 avoid these complications. The shank 304 extends into a tightly fitted bone tunnel such that the shank 304 is press fit into the cortex, or the hard exterior shell, of the bone. This increased amount of surface area between the shank and the bone cortex, as well as the protective sheath the shank 304 and the head 302 provide to the suture 318 at the bone's surface and the knotless locking mechanism, serve to anchor the implant and prevent the head 302 from cutting or subsiding into the bone tunnel, resulting in a more stable, longer lasting reinforcement construct. Any extra suture length 318 is completely trimmable such that the resulting suture is flush with the anchor head 302 and locked set screw 316, further preventing tissue irritation.

FIGS. 20-23 illustrate the details of the suture locking feature of the example of FIGS. 13-19. FIG. 20 provides an enlarged view of the features of the internal portion of the proximal portion 310 of the shank 304, and FIG. 21 provides a cross-sectional view of the proximal portion 310 of the shank 304 in receipt of the set screw 316. The proximal portion 310 of the shank has a receiver 330 having a tapered receiver thread 332, and the set screw 316 has a tapered external thread 334. Both the receiver thread 332 and the set screw thread 334 are rounded knuckle threads. In addition, the receiver 330/receiver thread 332 and the set screw 316/set screw thread 334 feature multiple discrete taper angles that transition proximally to distally to provide for progressive gripping and releasing of the suture 318 to provide a strong grip on the suture while reducing the risk of suture damage.

To address the taper angles in greater detail, FIGS. 22-23 illustrate the set screw 316 and the receiver 330 without their knuckle threading to better illustrate the gradual transitions of their tapers. The set screw 316 is cylindrical at a proximal portion 350, has a relatively small angled taper over its mid portion 352, and has a relatively large angled taper over its distal portion 354 which terminates in a rounded tip 364. The receiver 330 has a relatively large angled taper at a proximal portion 356, has a relatively small angled taper over its mid portion 358, and is cylindrical at its distal portion 360. When the set screw 316 and the receiver 330 are mated, they provide progressively less clearance between them from the proximal end of the anchor 300 to their mid portions and progressively more clearance between them from their mid portions distally to the end of the set screw 316.

This opposing tapered configuration of the set screw 316 versus the receiver 330 incorporates the principal of the Morse taper for mating components. The opposing conical shapes of the set screw 316 and the receiver 330 are closely matched or approximated in taper angle at their mid portions 352, 358, while the opposing shapes of the set screw 316 and the receiver 330 differ in taper angle at their proximate portions 350, 356 and their distal portions 354, 360. This arrangement causes the respective surfaces of the set screw 316 and the receiver 330 to achieve an interference fit about the suture 318 over the mid portions 352, 358 of the set screw 312 and the receiver 330, with gradual transitions proximally leading into and distally leading out of the interference fit. This gradual transition of compression forces applied to the suture 318 disposed between the set screw 316 and the receiver 330 leads to an enhancement in suture fixation/locking strength, and simultaneously reduces the risk of severing the suture 318 that is present with greater magnitudes of compression force transition.

In one embodiment, the mid portions 352, 358 of the set screw 316 and the receiver 330 are of the same length and aligned. In this embodiment, there are three zones or amounts of clearance between the set screw 316 and the receiver 330 progressing in three steps from a relatively large amount of clearance proximally to a relatively small amount of clearance over their mid portions to a relatively large amount of clearance distally.

In an alternate embodiment, and as shown in the example of FIGS. 20-23, the set screw 316 can be driven so that the beginning of its mid portion 352 is positioned distal of the beginning of the receiver mid portion 358, and the end of the set screw mid portion 352 is positioned proximal of the end of the receiver mid portion 358, as shown in FIG. 23. This arrangement results in five clearance zones 340, 342, 344, 346, and 348 for an even more gradual progression of gripping and releasing of the suture 316. Any number of taper angle steps may be provided on the set screw 316 and the receiver 330, and any arrangement of overlap or radius blending may be provided to produce any number of progressive clearance steps to transition proximally to distally from no grip to maximum grip to no grip on the suture, protecting the suture through the gradual increase and decrease of stress placed on the suture 318.

Referring to FIG. 23, the first zone 340 provides a maximum clearance proximally and the clearance decreases distally at the angular difference between the cylindrical proximal portion 350 of the set screw 316 and the relatively larger angle of the proximal portion 356 of the receiver 330. The second zone 342 clearance decreases distally at the angular difference between the cylindrical proximal portion 350 of the set screw 316 and the relatively smaller angle of the mid portion 358 of the receiver 330. The third zone 344 provides the least clearance and corresponds to where the mid portions 352, 358 of the set screw 316 and the receiver 330 coincide. The fourth zone 346 clearance increases distally at the angular difference between the relatively smaller angle of the mid portion 358 of the receiver 330 and the relatively larger angle of the distal portion 354 of the set screw 316. The fifth zone 348 provides the most clearance distally and the clearance increases distally at the angular difference between the relatively larger angle of the distal portion 354 of the set screw 316 and the cylindrical portion 360 of the receiver 330.

In the illustrative example of FIGS. 20-23, the set screw 316 taper is cylindrical in the first proximal portion 350, 10 degrees per side in the second mid portion 352, and 20 degrees per side in the distal portion 354. The receiver 330 taper is 20 degrees per side in the first proximal portion 356, 10 degrees per side in a second mid portion 358, and cylindrical at a third distal portion 360. The resulting relief tapers corresponding to the five zones 340, 342, 344, 346, 348 illustrated in FIG. 23, proximally to distally, are 20 degrees, 10 degrees, 0 degrees, 10 degrees, and 20 degrees. In this embodiment, the proximal ends 361, 363 of the receiver 330 and the set screw 316 are chamfered and the distal end 364 of the set screw 316 is rounded to further eliminate any sharp edges to further smooth the path of the suture and to provide easier starting of the screw.

While the embodiment of FIGS. 20-23 features opposing tapers on the set screw 316 and the receiver 330, it should be understood that the invention contemplates any appropriate tapering configuration that provides a gradual increase and decrease of compression forces applied, proximally to distally, to the interference fit of the suture 318 between the set screw 316 and the receiver 330. For example, the set screw 316 may be entirely cylindrical through its proximal, mid, and distal portions, maintaining the above described configuration of the receiver 330. In another example, the proximal, mid, and distal portions 350, 352, 354 of the set screw 316 may be angled to form an egg-like or football shape, while the proximal, mid, and distal portions 356, 358, 360 of the receiver 330 remain cylindrical.

The locking feature discussed in relation to FIGS. 20-23 provides both a knotless and reversible mechanism for locking out the suture 318 relative to the locking anchor 300. Because an interference fit between the suture 318, the set screw 316, and the receiver 330 provides the compression force required to secure the suture 318 in tension relative to the anchor 300, the locking feature provides a knotless fixation, thereby reducing the probability of bone and/or tissue abrasion and/or aggravation that is often caused by knotted fixations. Moreover, because the locking mechanism protects the integrity of the suture through the gradual increase and decrease of stress placed on the suture 318, as discussed above, the knotless fixation is truly reversible in that the set screw 316 may be rotationally inserted to lock out the suture 318 relative to the anchor 300 without damaging the suture 318 and/or risking its structural integrity. As a result, a surgeon may lock and unlock the suture 318 relative to the anchor 300 multiple times to achieve an optimal fixation while maintaining confidence in the quality of the ultimate knotless fixation.

Figure 1:
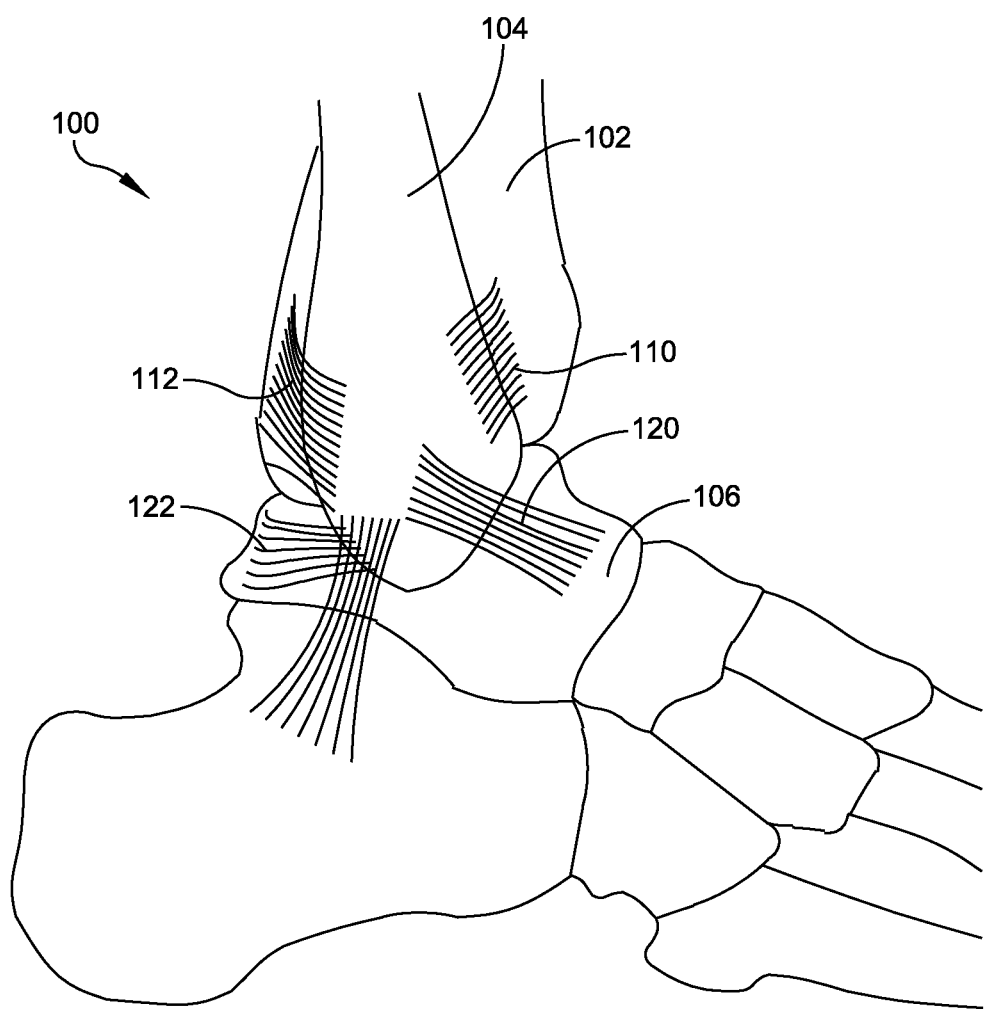
FIG. 1 illustrates a right view of a human ankle joint.
Figure 2:
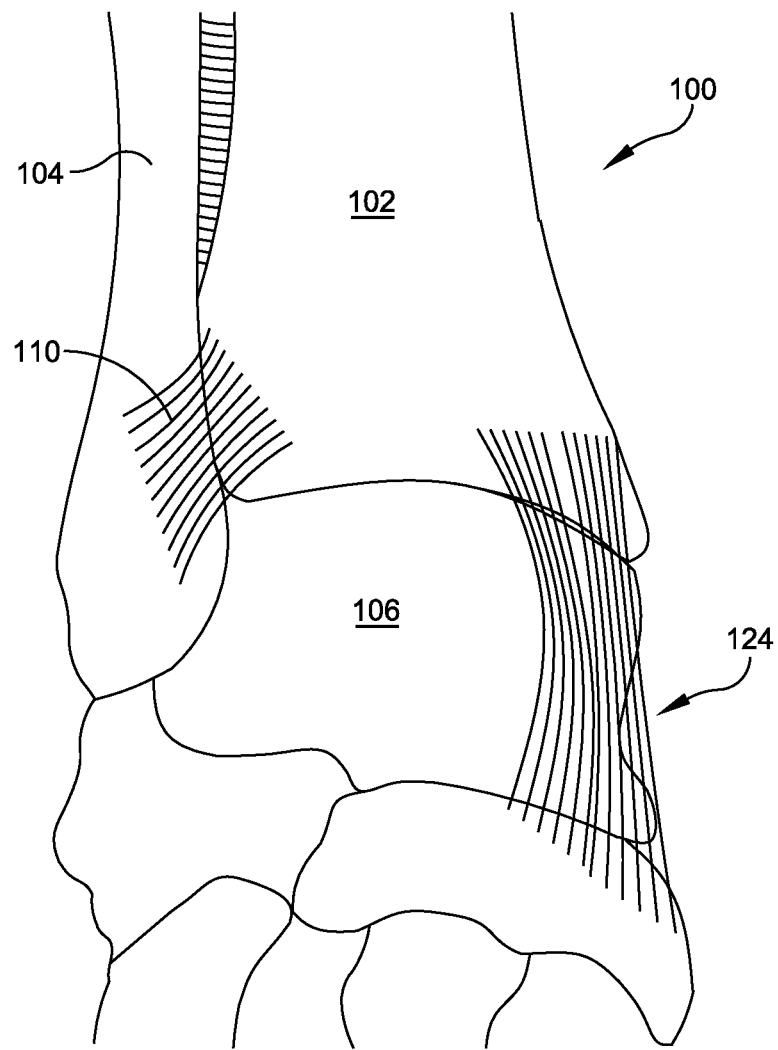
FIG. 2 illustrates a front view of a human ankle joint.
Figure 3:
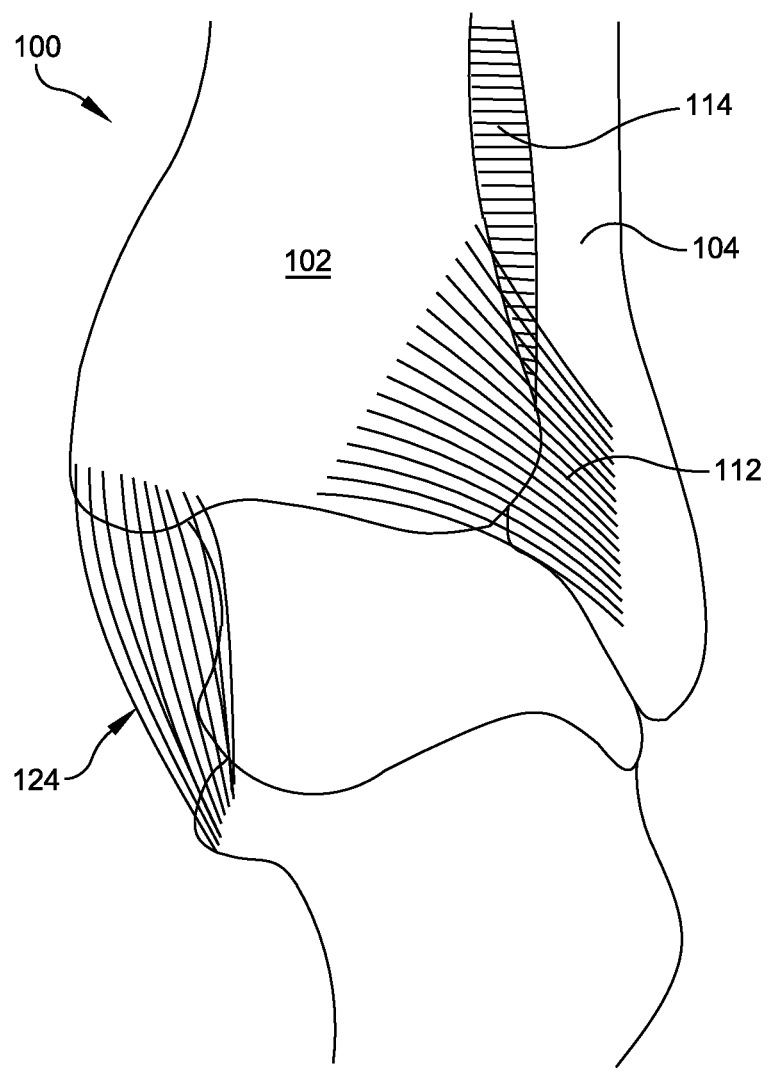
FIG. 3 illustrates a rear view of a human ankle joint.
Figure 24:
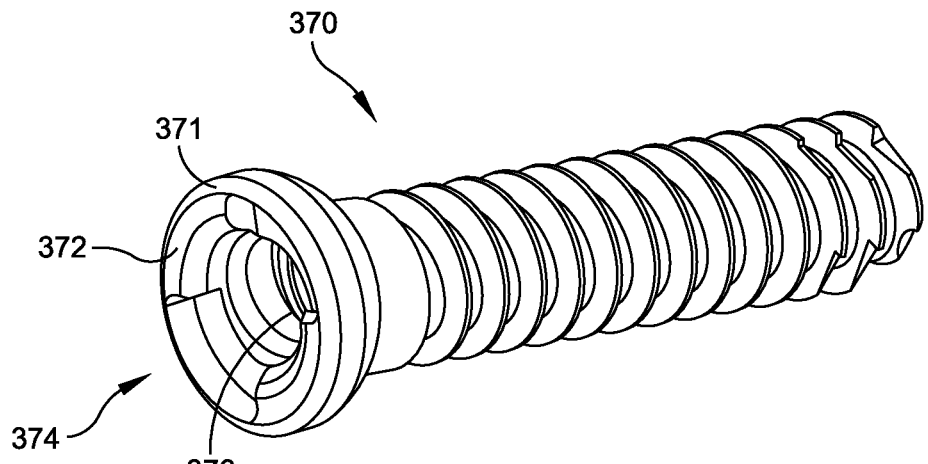
FIG. 24 illustrates a perspective view of one embodiment of a screw-type suture locking anchor having a countersunk head.
Figure 25:
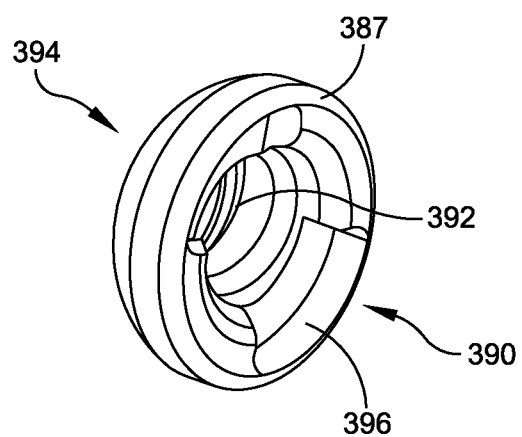
FIG. 25 illustrates a perspective view of one embodiment of a button-type suture locking anchor have a countersunk head.
Figures 26, 27:
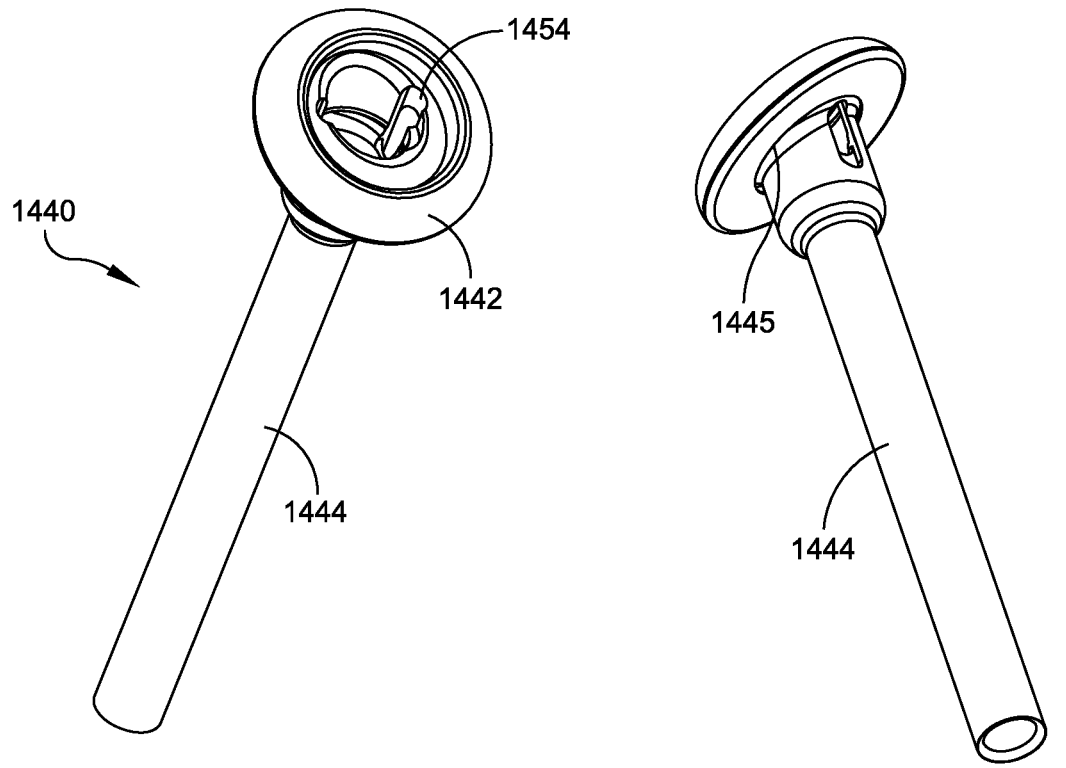
FIGS. 26-29 illustrate perspective, side, and cross-sectional views of one embodiment of a polyaxial suture locking anchor.
Figure 28:
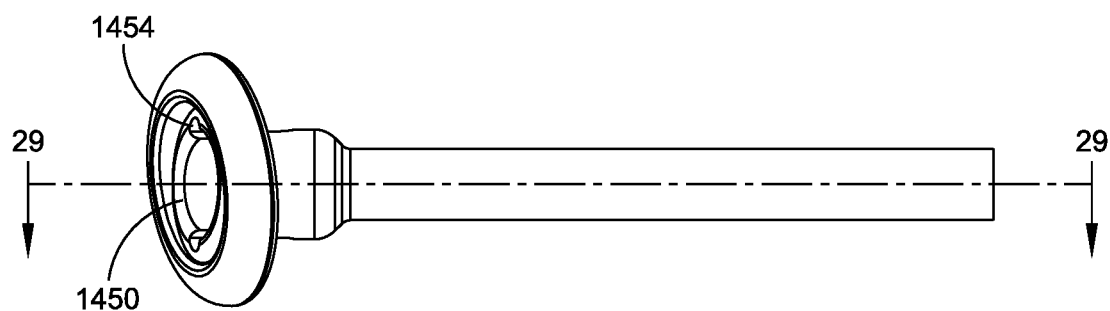
Figure 29:
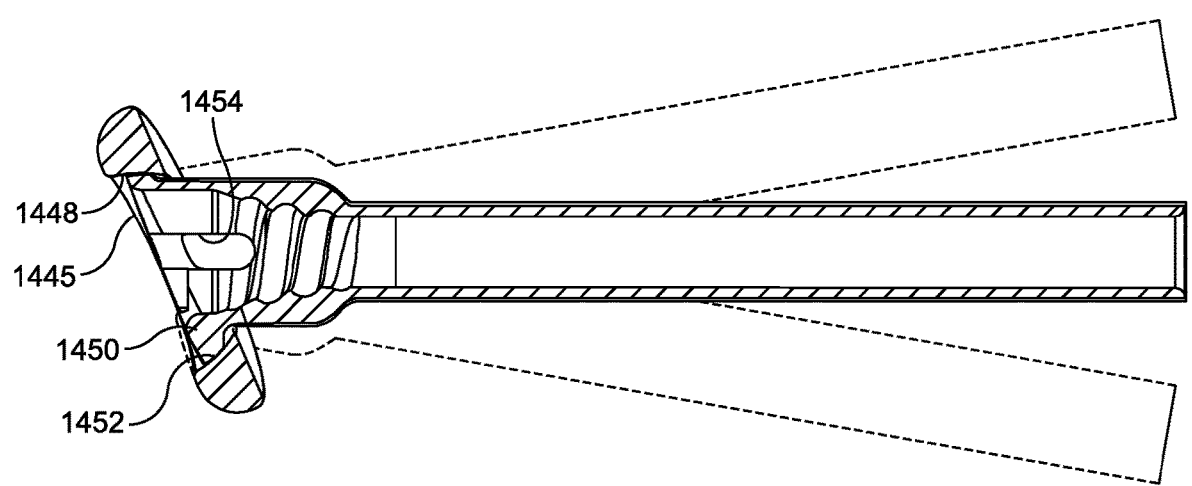

FIGS. 24-25 illustrate additional examples of suture locking anchors incorporating the tapered, knuckle-threaded suture-locking arrangement of FIGS. 20-23. In FIG. 24, an anchor 370 in the form of a bone screw has a proximal head 371 with an internal driver feature 372, an axial through hole 374, and a tapered threaded receiver 376 for receiving a set screw 316 like that shown in FIG. 21. FIG. 25 illustrates a suture locking anchor 394 in the form of a button with a proximal head 387 operable to seat in a spherical countersink in a bone plate. The anchor 394 includes an internal driver feature 396, and axial hole 390, and a tapered threaded receiver 392 for receiving a set screw like that shown in FIG. 25. Each of the respective proximal heads 371, 387 of the anchors 370, 394 may be countersunk such that they are configured to seat within, and reside flush with a surface of, a bone plate positioned upon and anchored to either the tibia 102 or the fibula 104 (FIGS. 1-3).

Figure 16:
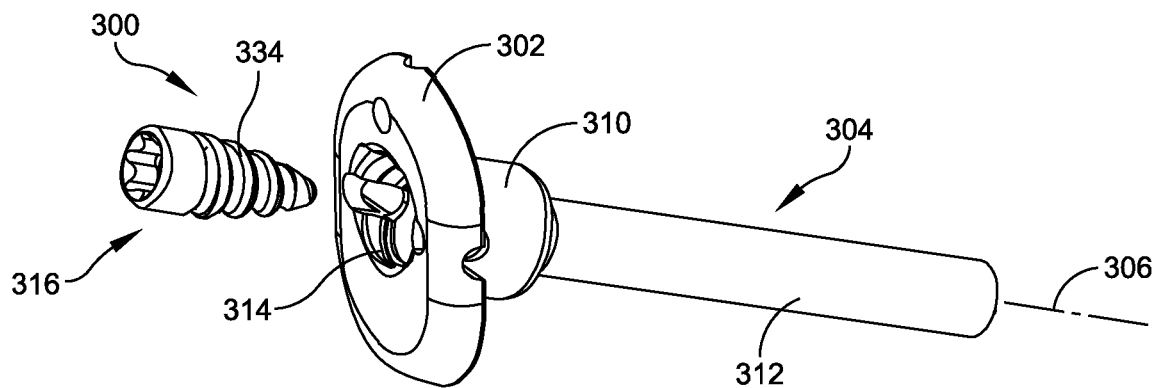
Figure 17:
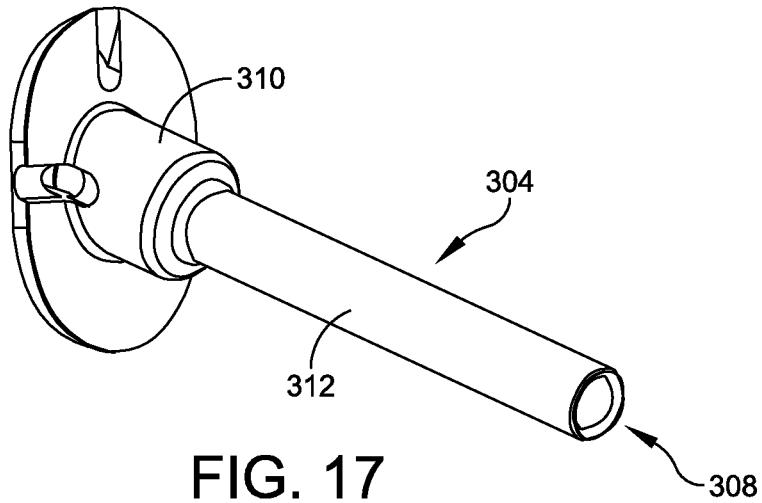
Figures 18, 19:
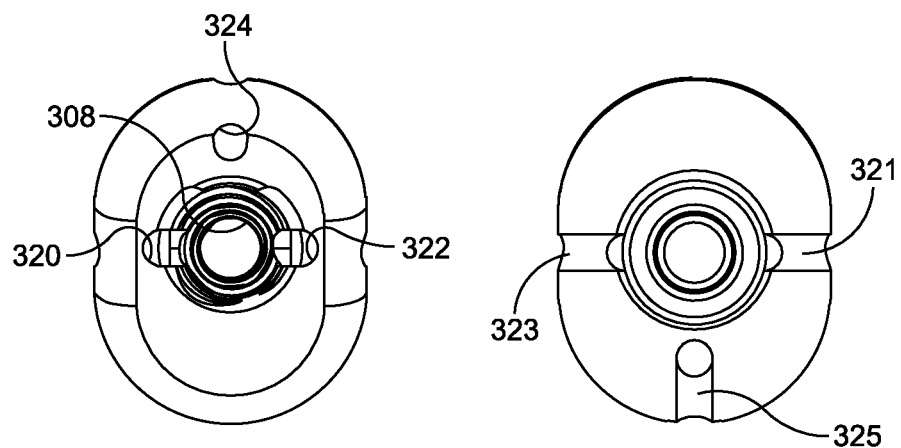

FIGS. 26-29 illustrate an example of a polyaxial suture locking anchor 1440 similar to the anchor 300 of FIG. 16. However, the anchor of the example of FIGS. 26-29 is a two-piece anchor having a separate washer 1442 and shank 1444. The washer has a hole 1445 formed through it and a spherical seat 1448 formed adjacent the hole. The shank 1444 has a head 1450 with a spherical seat 1452 on its undersurface, adjacent the shank 1444. The spherical seats 1448 and 1452 engage and permit the washer 1442 to assume a range of angles relative to the shank so that when the shank 1444 is inserted into a tunnel in a bone and advanced so that the washer is abutting the bone surface, the washer can angulate to match the angle between the bone tunnel and the bone surface. The adjustable polyaxial relationship between the shank 1444 and washer 1442 permits the washer 1442 to lie close to the bone in a low-profile manner.

Figure 30:
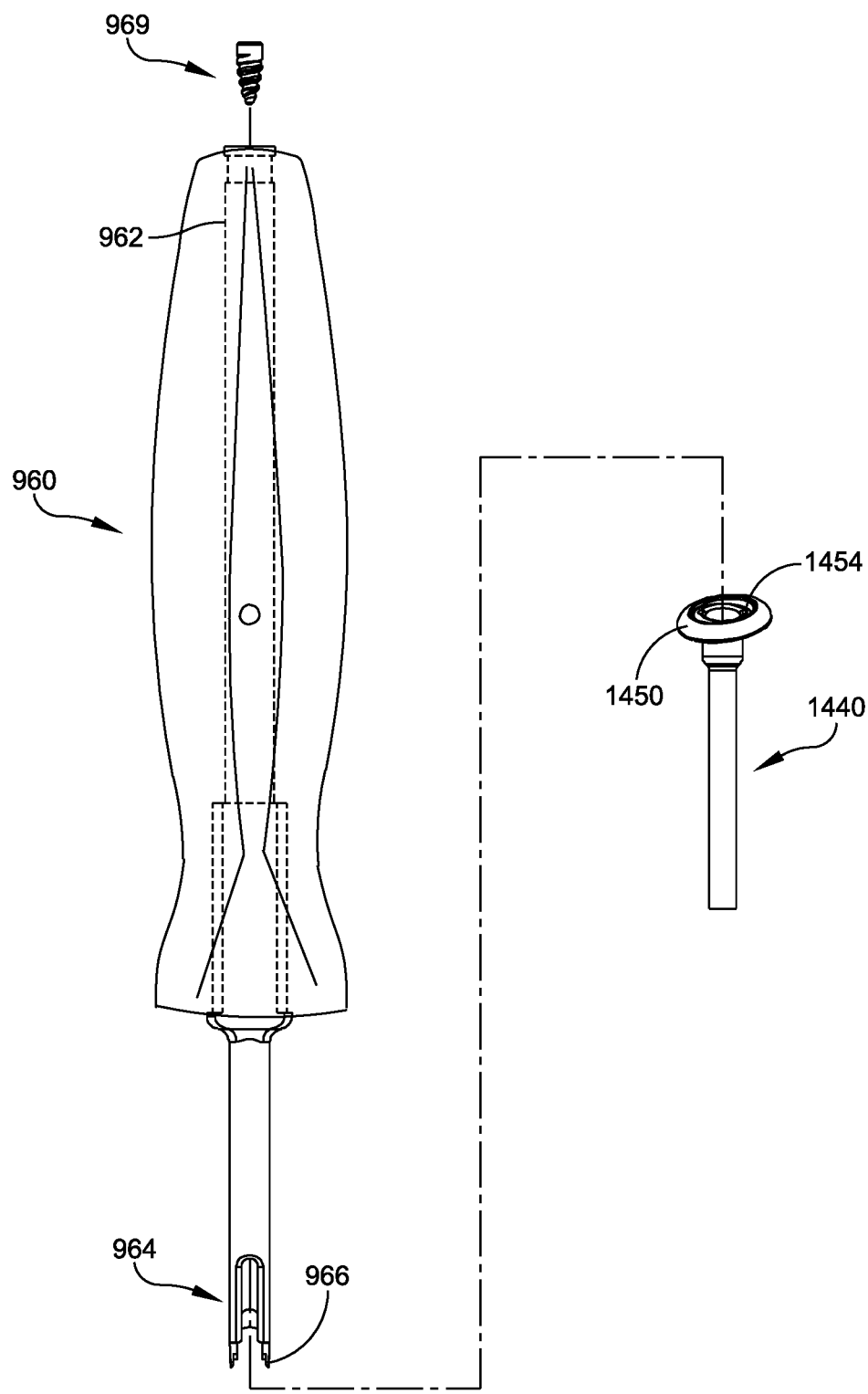
FIG. 30 illustrates an exploded view of one embodiment of a counter-torque anchor driver instrument in use with the suture locking anchor of FIGS. 13-19.

FIG. 30 illustrates a counter-torque instrument 960 having a hollow shaft 962 and an anchor engaging end 964. The counter-torque instrument 960 may be used to knotlessly lock a suture via an interference fit between a set screw such as set screw 969 and a number of appropriate anchors such as, for example, anchors 300, 370, 394, and 1440, discussed above. Focusing on anchor 1440 for purposes of example, the anchor engaging end 964 of the counter-torque instrument 960 includes spaced apart prongs 966. The prongs 966 are engageable with corresponding grooves 1454 formed in the head 1450 of the shank 1444 of the anchor 1440. This engagement provides a counter-torque force that holds the shank 1444 stationary and prevents the shank 1444 from rotating when the set screw 969 is driven or torqued down into the anchor 1440 using an appropriate set screw driver inserted through the hollow shaft 962. Thus, the surgeon may drive the set screw 969 into the anchor 1440 without fear of inadvertently torqueing or impacting the desired angular relationship between the shank 1444 and the washer 1442 of the polyaxial anchor 1440, which permits the washer 1442 to lie flush against the bone, as discussed above. This ability to counter any torsional forces generated by the driver and the set screw 969 upon the washer 1442 and/or the shank 1444 of the anchor 1440 is satisfying for the surgeon and results in more effective anchor placement and locking.

Intra Joint Constructs and Operative Sequences

FIGS. 31-54 illustrate a number of methods of according to examples of the invention in use to internally stabilize or reinforce ligaments across bone joints and/or to stabilize bone portions across bone fractures.

Figure 31:
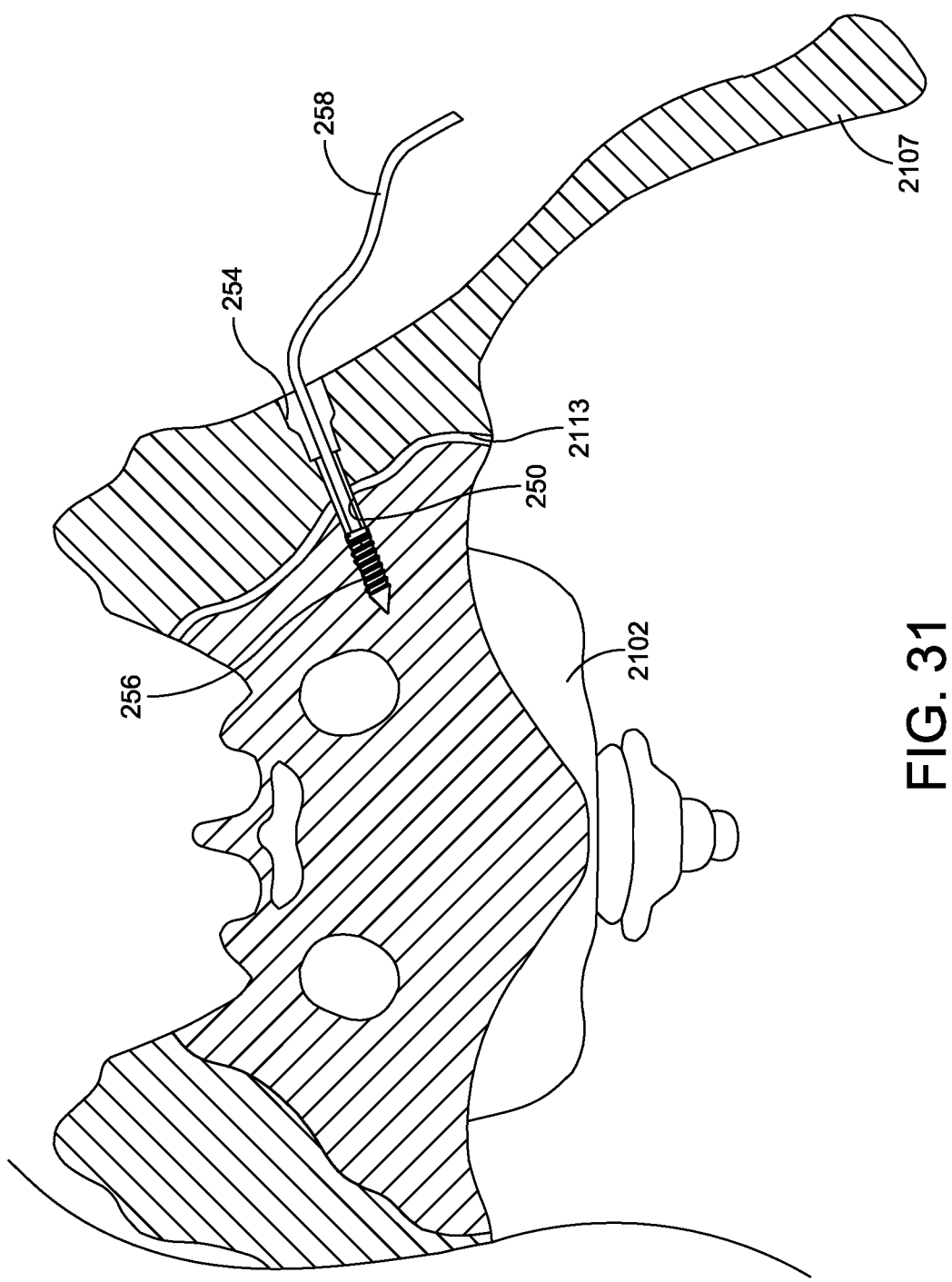
FIGS. 31-33 show partial sectional views through the sacrum parallel to the anatomic transverse plane of the pelvis and illustrate the steps of an operative sequence for reinforcing a sacroiliac fracture joint via a blind-hole bone tunnel using embodiments of the disclosed devices.
Figure 32:
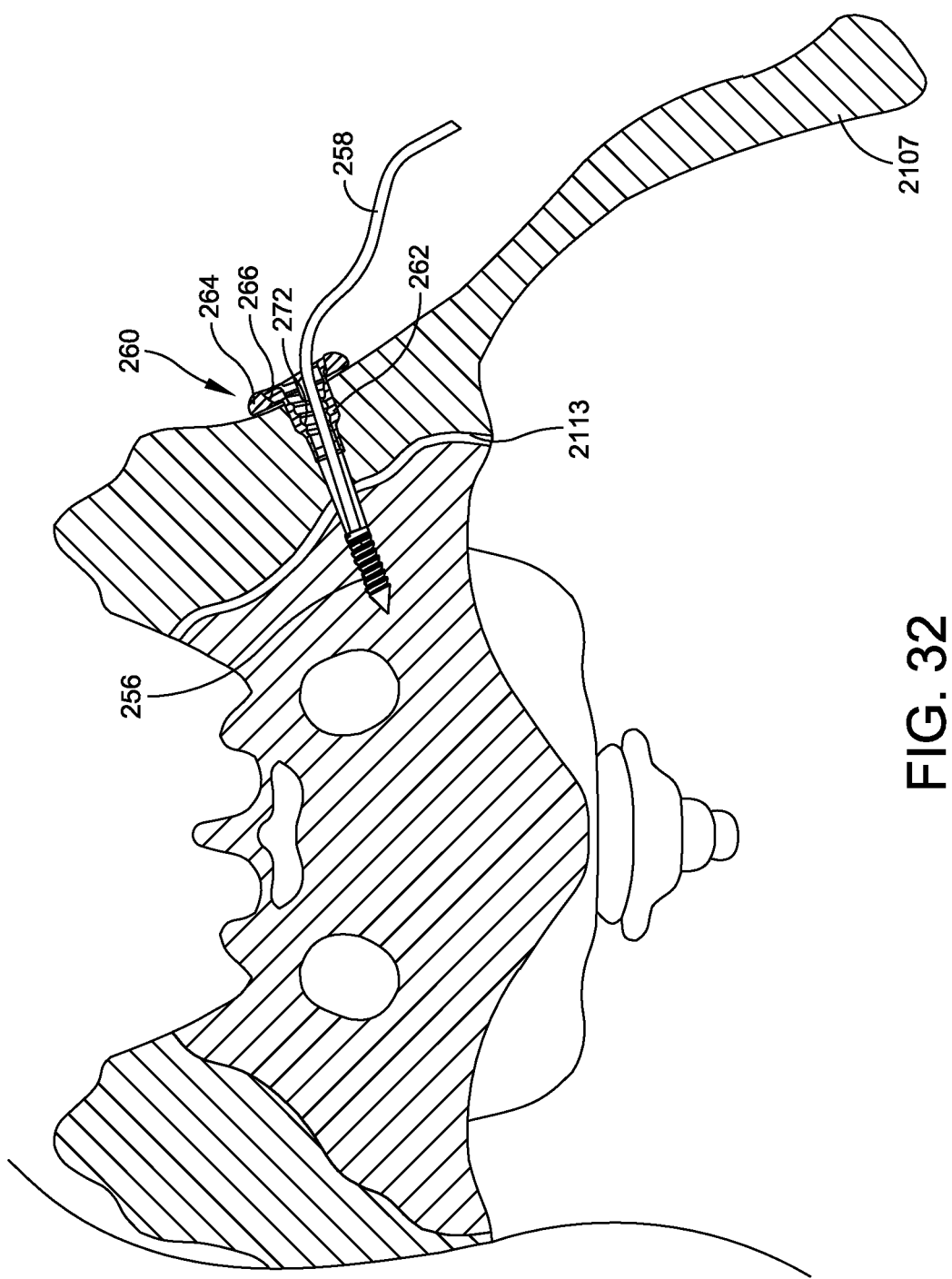
Figure 33:
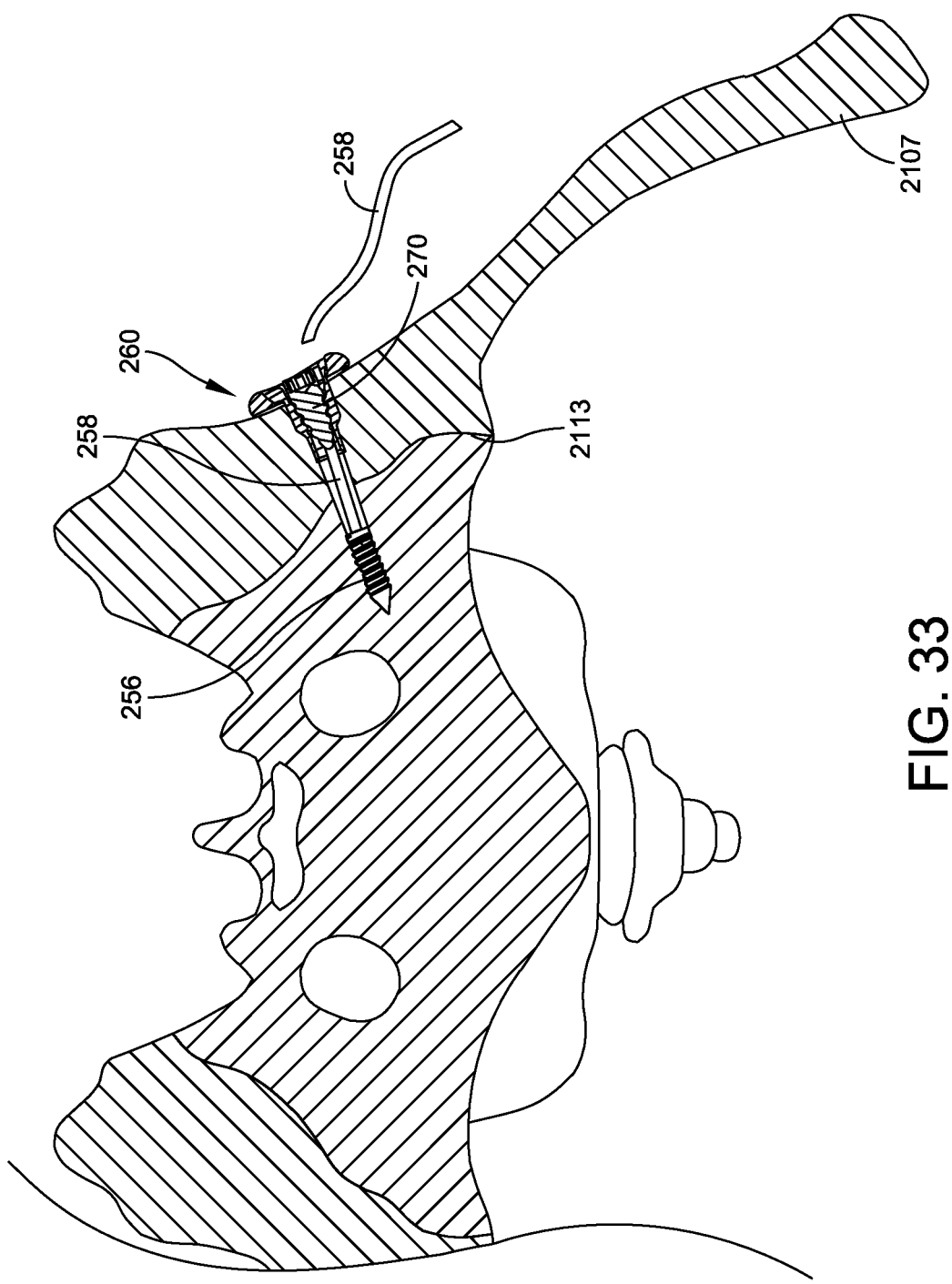
Figure 34:
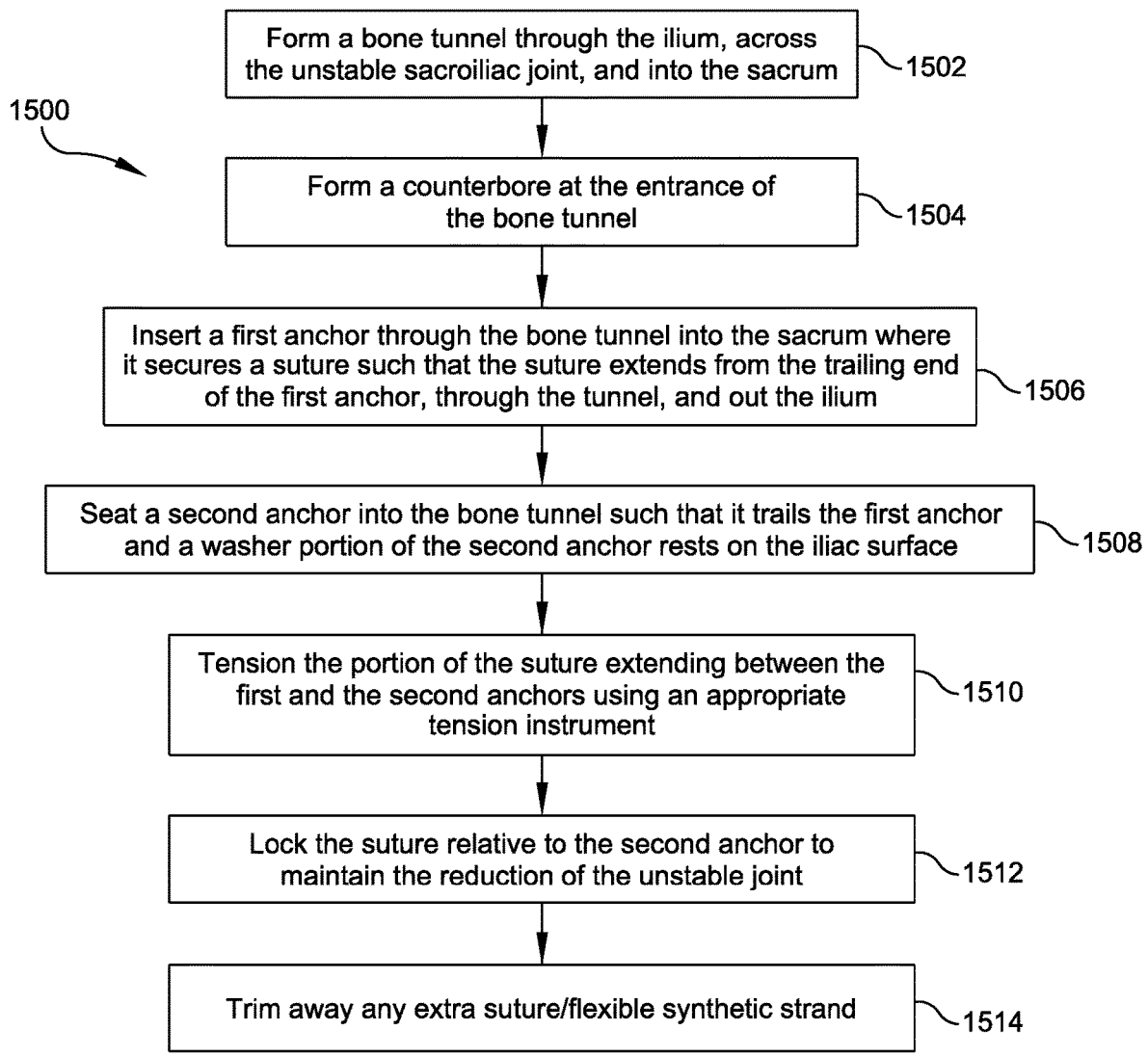
FIG. 34 provides a flowchart detailing the operative sequence illustrated by FIGS. 31-33.

FIGS. 31-33 illustrate a repair construct in which exemplary devices are used to reinforce a fractured bone joint via a "blind hole" bone tunnel, into which a first anchor is fit, and a second anchor trails the first anchor within the blind-hole tunnel. More specifically and in one embodiment, exemplary devices are in use to repair a sacroiliac joint 2113 to stabilize the pelvis after an anterior-posterior compression fracture. FIG. 34 provides a flowchart depicting an exemplary method 1500 of reinforcing the sacroiliac joint 2113 according to the steps illustrated in FIGS. 31-33.

Referring to FIG. 31, a bone tunnel 250 is formed through the ilium 2107, across the unstable sacroiliac joint 2113, and into the sacrum 2102 (FIG. 34, 1502). A counterbore 254 is formed at the entrance of the tunnel 250 on the surface of the ilium 2107 (FIG. 34, 1504). A first anchor 256 is inserted through the tunnel 250 into the sacrum 2102 where it secures a flexible strand such as a suture 258 (FIG. 34, 1506). The flexible strand 258 extends from the trailing end of the first anchor 256 through the tunnel 250 and out the ilium 2107.

Referring to FIG. 32, the flexible strand 258 is placed through a second anchor 260 which is seated on the ilium 2107 (FIG. 34, 1506-1508). The second anchor 260 includes a tubular portion 262 that extends into the tunnel countersink 254 and a washer portion 264 that rests on the iliac surface. In the example of FIGS. 31-33, the tubular portion 262 and the washer portion 264 are separate pieces that engage on a cylindrical seat 266 to permit them to articulate relative to one another to adaptively align with the bone surface and tunnel 250. The anchors and the flexible synthetic strand or suture may include the examples disclosed above in FIGS. 13-29 and in FIGS. 5-13 of US patent application Ser. No. 15/641,592, entitled "EXTRA JOINT STABILIZATION CONSTRUCT" and co-filed with this application on Jul. 5, 2017.

To tension the portion of the suture 258 extending between the anchors 256, 260 (FIG. 34, 1510), the end of the suture 258 may be pulled using an appropriate tension instrument of the type disclosed, for example, in FIGS. 12-15 of US patent application Ser. No. 15/642,053, entitled "COMPRESSION AND TENSION INSTRUMENTS AND METHODS OF USE TO REINFORCE LIGAMENTS" and co-filed with this application on Jul. 5, 2017. As a result, and as shown in FIG. 33, the unstable sacroiliac joint 2113 is reduced. The suture 258 may then be locked relative to the second anchor to maintain the reduction (FIG. 34, 1512). To lock, a locking set screw 270 may be advanced through a central cannulation in the tension instrument and threaded into internal threads 272 formed in the second anchor 260, thereby locking the suture 258 relative to the second anchor 260 via an interference fit between the set screw 270 and the internal threads 272 of the anchor 260. The tensioner may then be removed, and any excess length of the suture 258 may be trimmed away such that the suture 258 is flush with the anchor 260 (FIG. 34, 1514).

The sacroiliac joint 2113 repair discussed in FIGS. 31-34 may be used in place of or in conjunction with prior art iliosacral screws. The flexible construct shown in FIG. 33 is advantageous in that it provides controlled reduction of the unstable joint after placing the anchors. The joint may be tested while the tensioner is still attached, and the tension adjusted to the desired stability. The tension in the joint may be adjusted to any desired value prior to locking the suture 258 to the second anchor 260. The locking mechanism is knotless and reversible allowing for subsequent readjustment and relocking if needed and/or desired. The construct places a continuous and uninterrupted flexible member (e.g., the suture/flexible synthetic strand 258) across the joint 2113, which makes it less susceptible to failure than a rigid implant that may experience fatigue failure.

The construct of FIG. 33 may be applied at any desired location relative to the joint. The construct location may be more anterior or posterior or more superior or inferior. The first anchor 256 may be set more deeply into the sacrum. The first anchor 256 may be secured into the cortical bone on the opposite side of the sacrum from the unstable sacroiliac joint such that the suture 258 spans the sacrum. Multiple constructs may be applied to achieve a desired level of stability. Multiple constructs may be spaced apart superior-to-inferior and/or anterior-to-posterior. Further, while FIGS. 31-34 refer to the reinforcement of a sacroiliac joint 2113 to stabilize the pelvis after an anterior-posterior compression fracture, similar methods and devices may be employed as appropriate to stabilize a variety of bone joints within the body.

Figure 35:
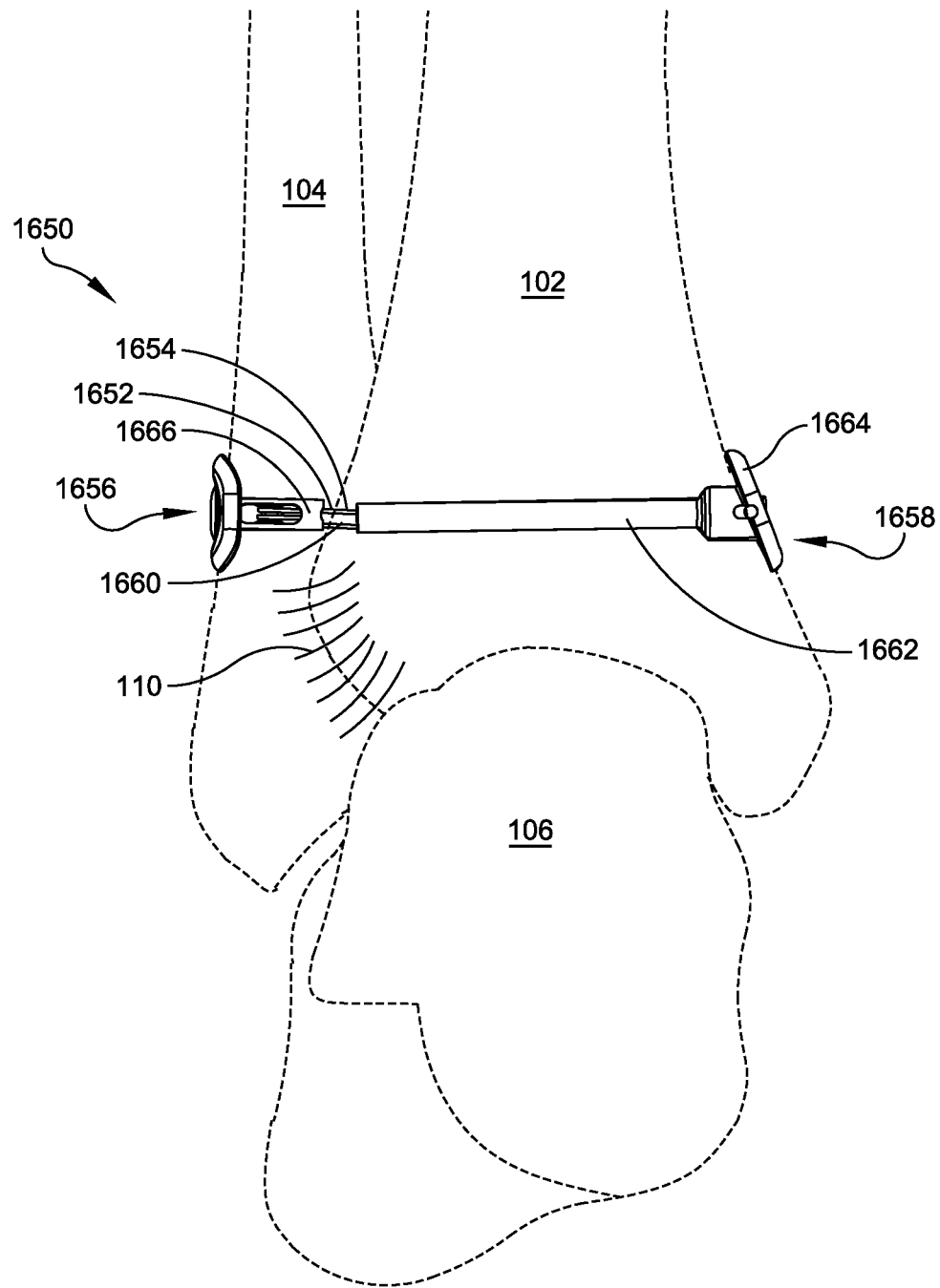
FIG. 35 illustrates a side view of one embodiment of a syndesmosis reduction construct for an anterior inferior tibiofibular ligament (AITFL) using embodiments of the disclosed devices.

FIG. 35 illustrates exemplary devices in use to reinforce a ligament that extends across a joint between two bones. More specifically and in one embodiment, FIG. 35 illustrates a syndesmosis reduction construct 1650 for an anterior inferior tibiofibular ligament (AITFL) 110, while FIG. 36 provides a flowchart depicting an exemplary method 1600 of reinforcing the AITFL 110, as illustrated in FIG. 35.

Figure 36:
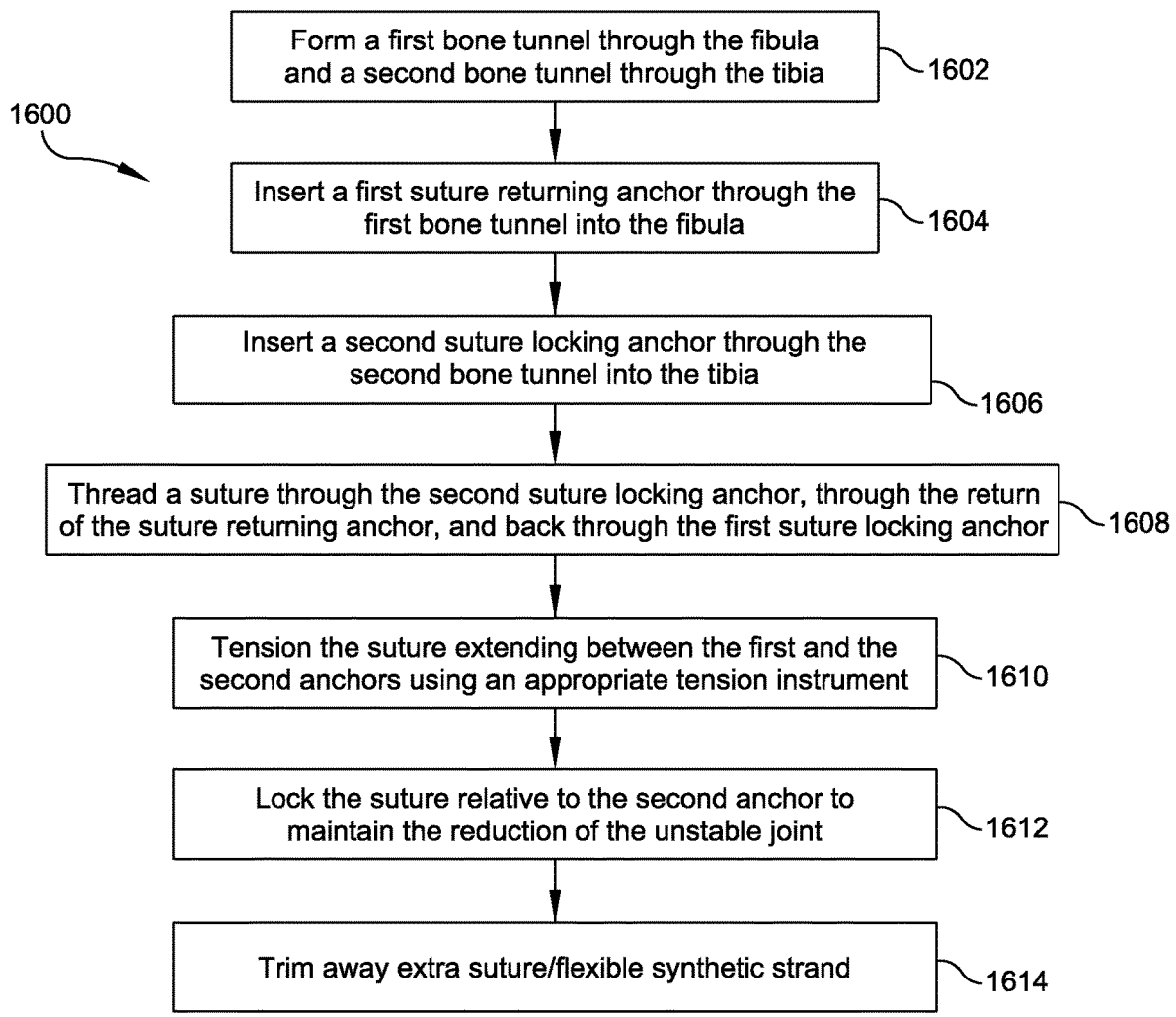
FIG. 36 provides a flowchart depicting an exemplary operative method for forming the syndesmosis reduction construct of FIG. 35.

Referring to FIG. 35, first a bone tunnel 1652 is formed through the fibula 104, and a second, coaxial and adjacent tunnel 1654 is formed within the tibia 102 (FIG. 36, 1602). A first suture returning anchor 1656 is inserted through the first tunnel 1652 into the fibula 104 (FIG. 36, 1604). The suture returning anchor may be, for example, the polyaxial suture returning anchor 920, discussed above in relation to FIGS. 6-12. A second suture locking anchor 1658 is inserted through the second tunnel 1654 into the tibia 102 (FIG. 36, 1606). The suture locking anchor may include, for example, the suture locking embodiments disclosed above in relation to FIGS. 13-29.

A flexible strand such as a suture 1660 may be threaded from the right through the second suture locking anchor 1658, returned via the first suture returning anchor 1656, and back through the first suture locking anchor 1658 (FIG. 36, 1608), such that both ends of the suture 1660 extend from the second suture locking anchor 1658, which is seated on the tibia 102.

The second anchor 1658 includes a tubular portion 1662 that extends into the tunnel 1654 and a washer portion 1664 that rests on the tibial surface. In the example of FIG. 35, the tubular portion 1662 and the washer portion 1664 are separate pieces that engage on a cylindrical seat to permit them to articulate relative to one another to adaptively align with the tunnel 1654 and the surface of the tibia 102, respectively.

To tension the suture 1660 extending between the first and second anchors 1656, 1658 (FIG. 36, 1610), the ends of the suture 1660 may be pulled using an appropriate tension instrument of the type disclosed, for example, in FIGS. 12-15 of US patent application Ser. No. 15/642,053, entitled "COMPRESSION AND TENSION INSTRUMENTS AND METHODS OF USE TO REINFORCE LIGAMENTS" and co-filed with this application on Jul. 5, 2017. As a result, and as shown in FIG. 35, the syndesmosis joint is reduced such that the ligament 110 is reinforced. The suture 1660 may then be locked relative to the second suture locking anchor 1658 to maintain the reduction (FIG. 36, 1612). The tensioner may then be removed, and any excess length of the suture 1660 may be trimmed away such that the suture 1660 is flush with the anchor 1658 (FIG. 36, 1614).

Like the sacroiliac joint repair of FIGS. 31-34, the ligament reinforcement construct 1650 discussed in relation to FIGS. 35-36 provides a continuous, uninterrupted strand from one anchor to the other along the direction of the native ligament, as well as a controlled reduction of the unstable joint after placing the anchors. The joint may be tested while the tensioner is still attached, and the tension adjusted to the desired stability. The tension may be adjusted prior to locking and readjusted as needed and/or desired. The construct places a continuous, uninterrupted flexible member (e.g., the suture 1660) across the joint, which makes it less susceptible to failure than a rigid implant that may experience fatigue failure.

Figure 37:
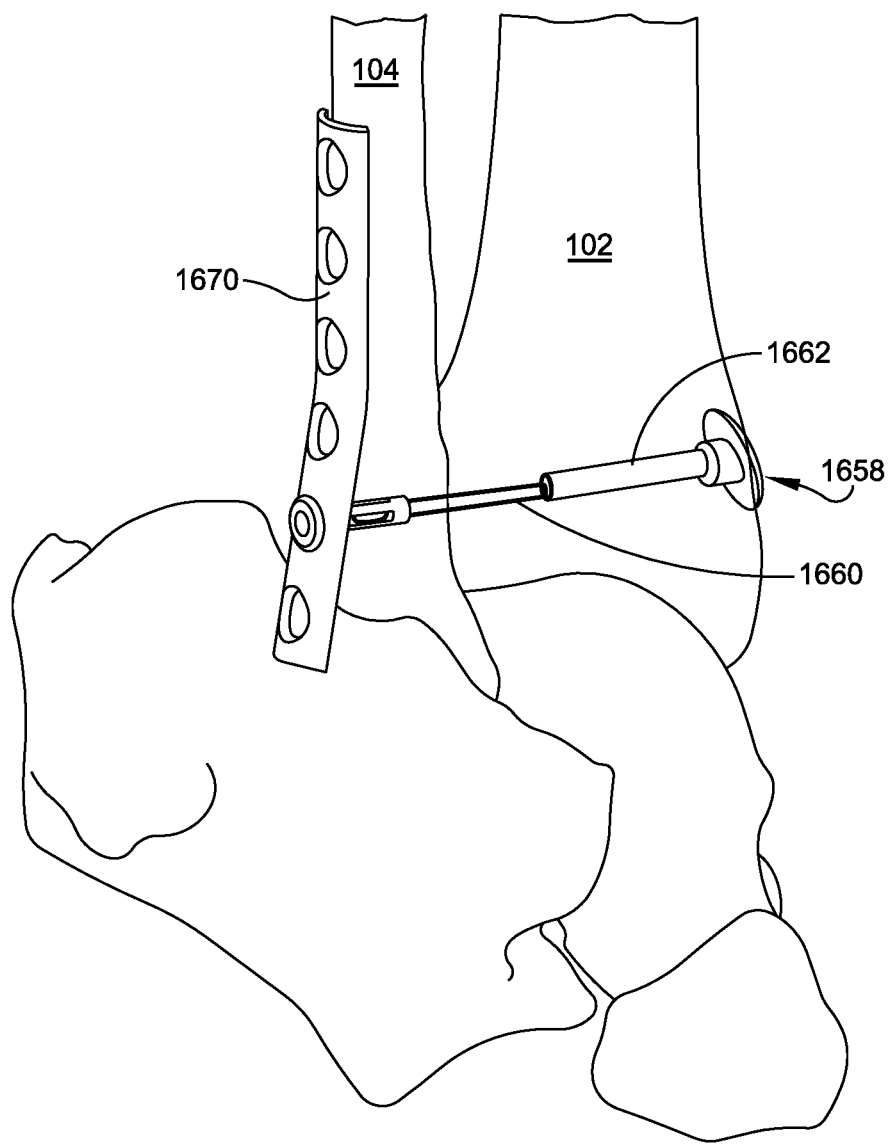
FIG. 37 illustrates a side view of another embodiment of a syndesmosis reduction construct for an AITFL using embodiments of the disclosed devices and incorporating a bone plate.

The construct 1650 of FIG. 35 may be applied at any desired location relative to the joint/ligament. The construct location may be more anterior or posterior (e.g., could be constructed to reinforce the PITFL 112) or more superior or inferior. Multiple constructs may be applied to achieve a desired level of stability. Multiple constructs may be spaced apart superior-to-inferior and/or anterior-to-posterior. Further, while FIGS. 35-36 refer to the reinforcement of the AITFL 110, similar methods and devices may be employed as appropriate to reinforce any ligament within the body. As shown in FIG. 37, the exemplary construct may be used in conjunction with a bone plate 1670.

Focusing on FIG. 35, the tubular portion 1662 of the anchor 1658 serves as a suture sleeve that extends toward an end of the second bone tunnel 1654 and an inner surface of the tibia 102. Likewise, a tubular portion 1666 of the first anchor 1656 serves as a suture sleeve that extends toward an end of the bone tunnel 1652 and an inner surface of the fibula 104. The tubular portions/sheaths 1662, 1666 provide bone tunnel protection and limit transverse movement, or suture wipering, of the suture 1660 to within the space between the sleeves 1662, 1666. If the sleeves 1662 and 1666 extend to the end of the bone tunnel 1654/surface of the tibia 102 and the end of the bone tunnel 1652/surface of the fibula 104, respectively, then the suture 1660 is flexible only over a span of the natural ligament, and transverse movement or suture wipering is limited to the length of the span of the natural ligament across the joint between the bones (e.g., 1-2 mm). Because suture wipering over time abrades the bone within the bone tunnel and about the bone tunnel edges, utilizing anchors featuring hollow shafts/sheaths to contain the suture in turn reduces the abrasion of the bone caused by the suture. The further the tubular portions/sleeves 1662, 1666 extend toward the other bone, the less such suture wipering and resulting abrasion can occur.

Figure 38:
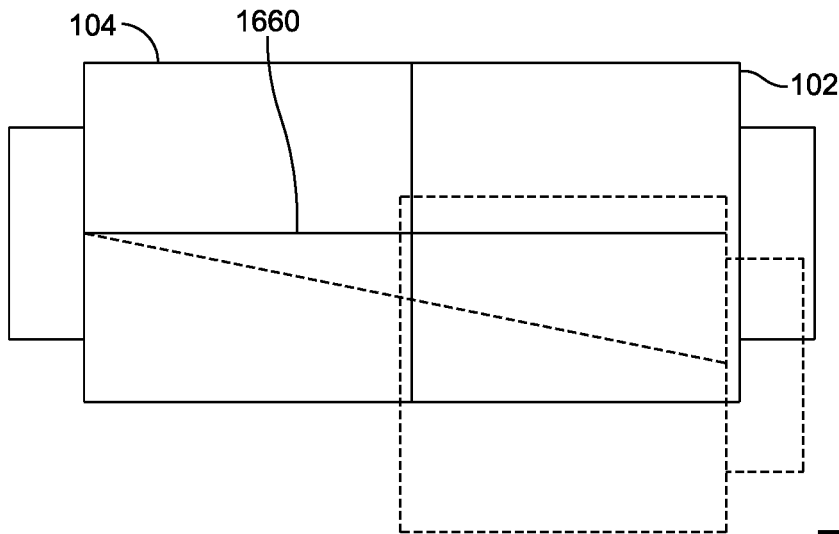
FIGS. 38-40 provide graphic depictions of the syndesmosis reduction construct of FIG. 35, each figure showing progressively longer anchor sleeves that decrease a free span of suture extending between the sleeves.
Figure 39:
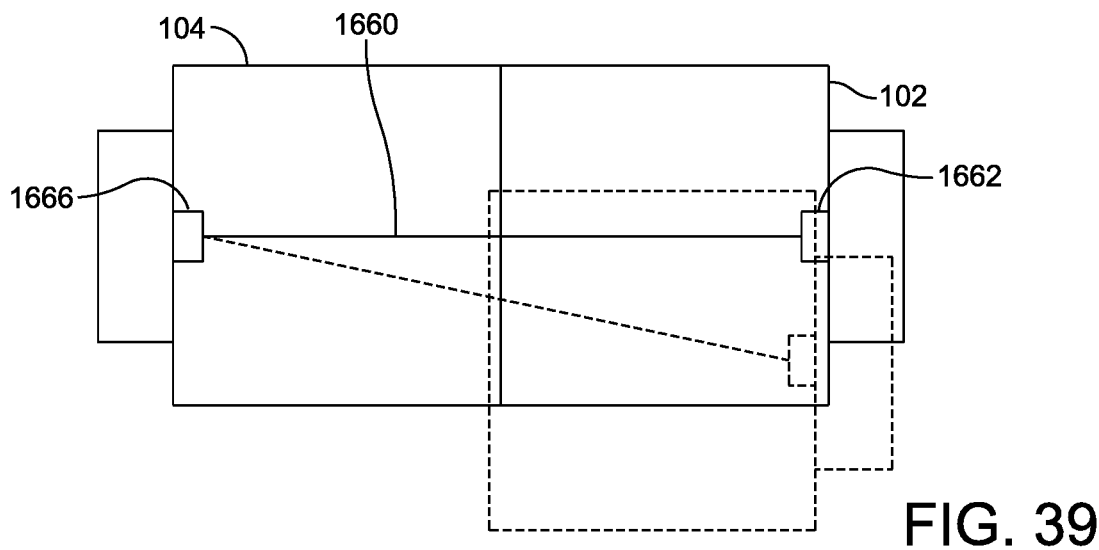
Figure 40:
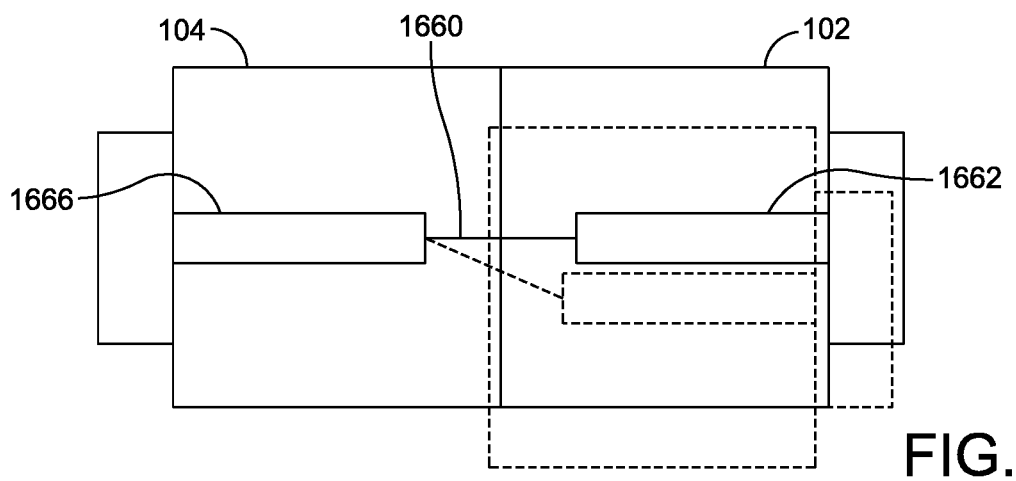

To demonstrate, FIGS. 38-40 graphically depict that for a given amount of construct compliance—which includes suture stretch, slip, compression of the bones and the bone interface, and other factors, all represented here by a constant amount of bone overlap shown in dashed line—increasing the lengths of the tubular anchor sleeves 1662, 1666 decreases the amount of suture cutting or wipering that can occur. In other words, as the free span of the suture 1660 between the tubes/sleeves 1662, 1666 decreases from that shown in FIG. 38 to that shown in FIG. 40, there is less possible deviation in the relative positions of the bones 102, 104 and less cutting into the bones 102, 104 by the suture 1660.

Figure 41:
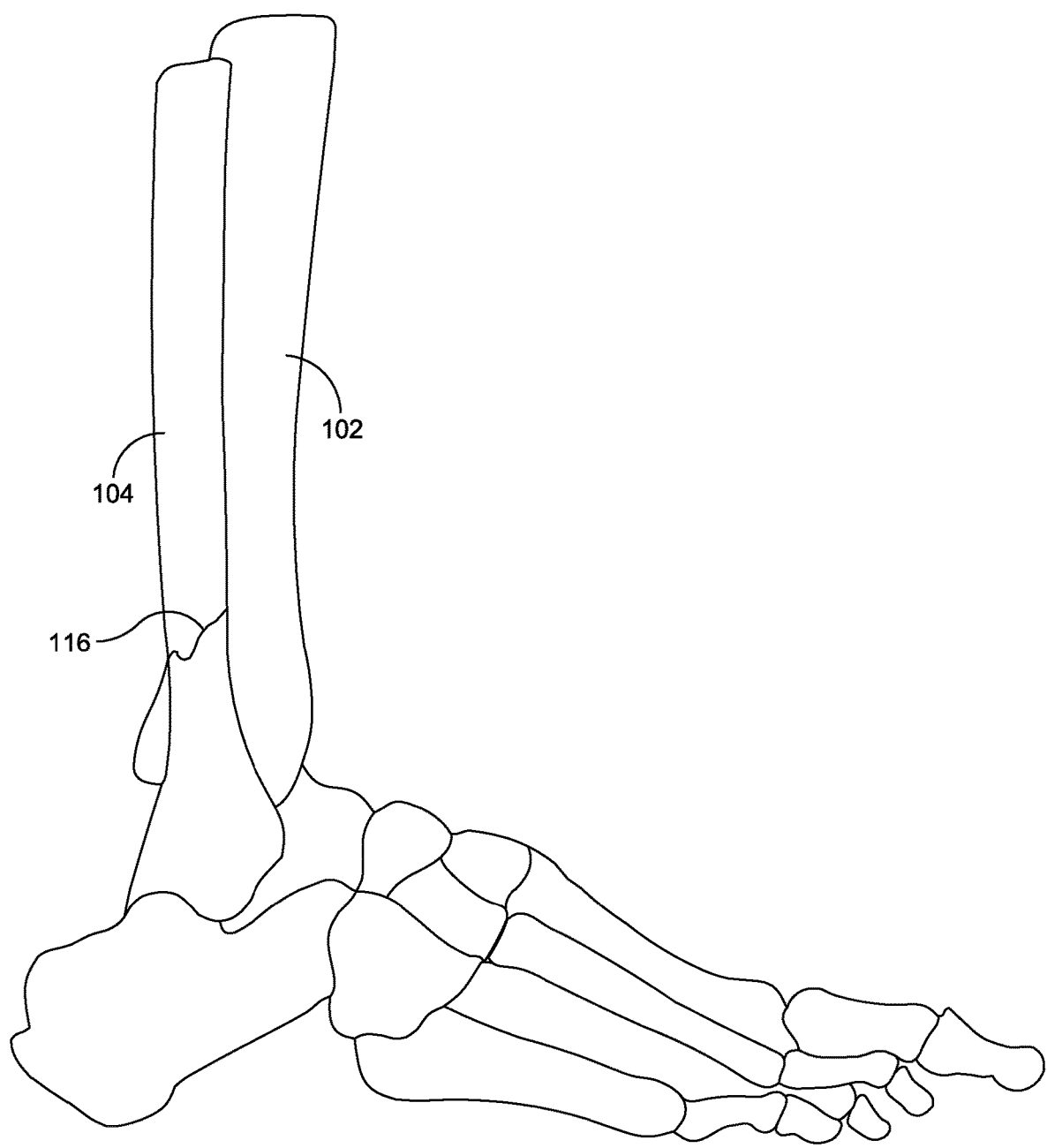
FIG. 41 illustrates a lateral view of a human ankle having a fracture of the fibular shaft.
Figure 47:
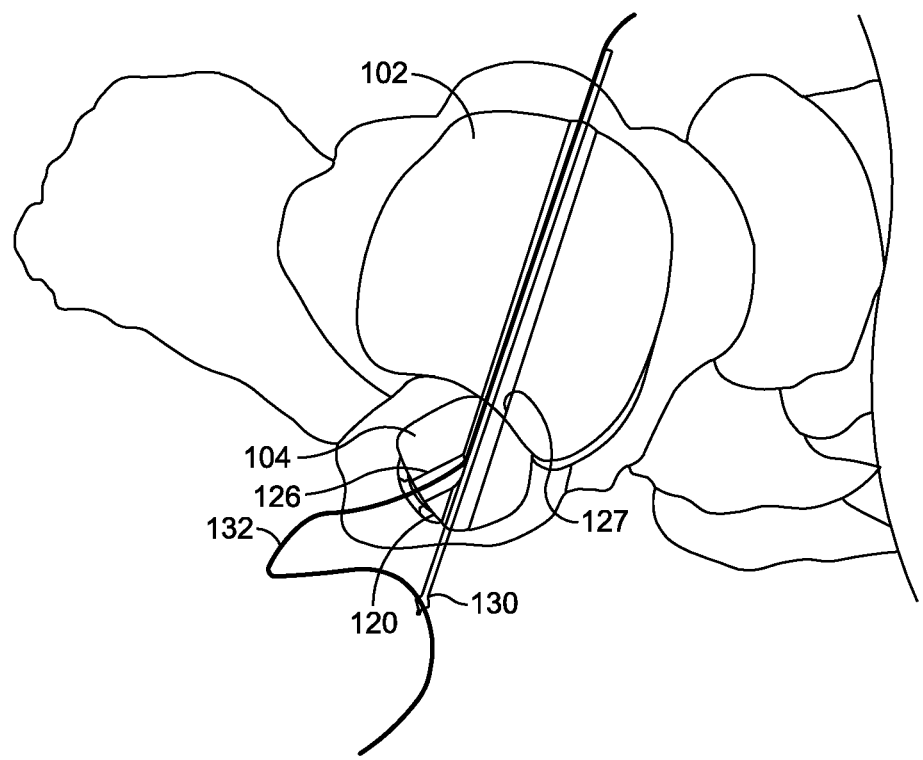
Figure 48:
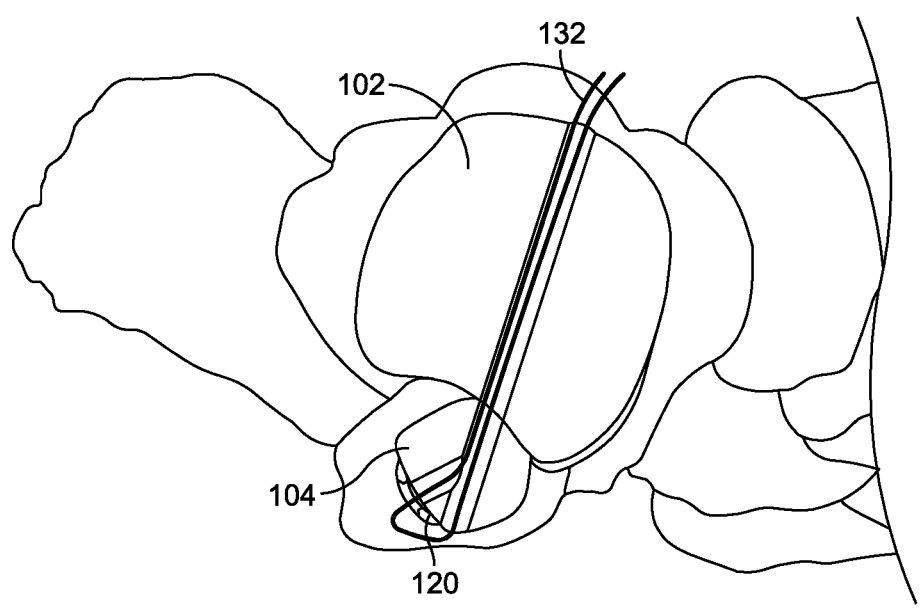
Figure 49:
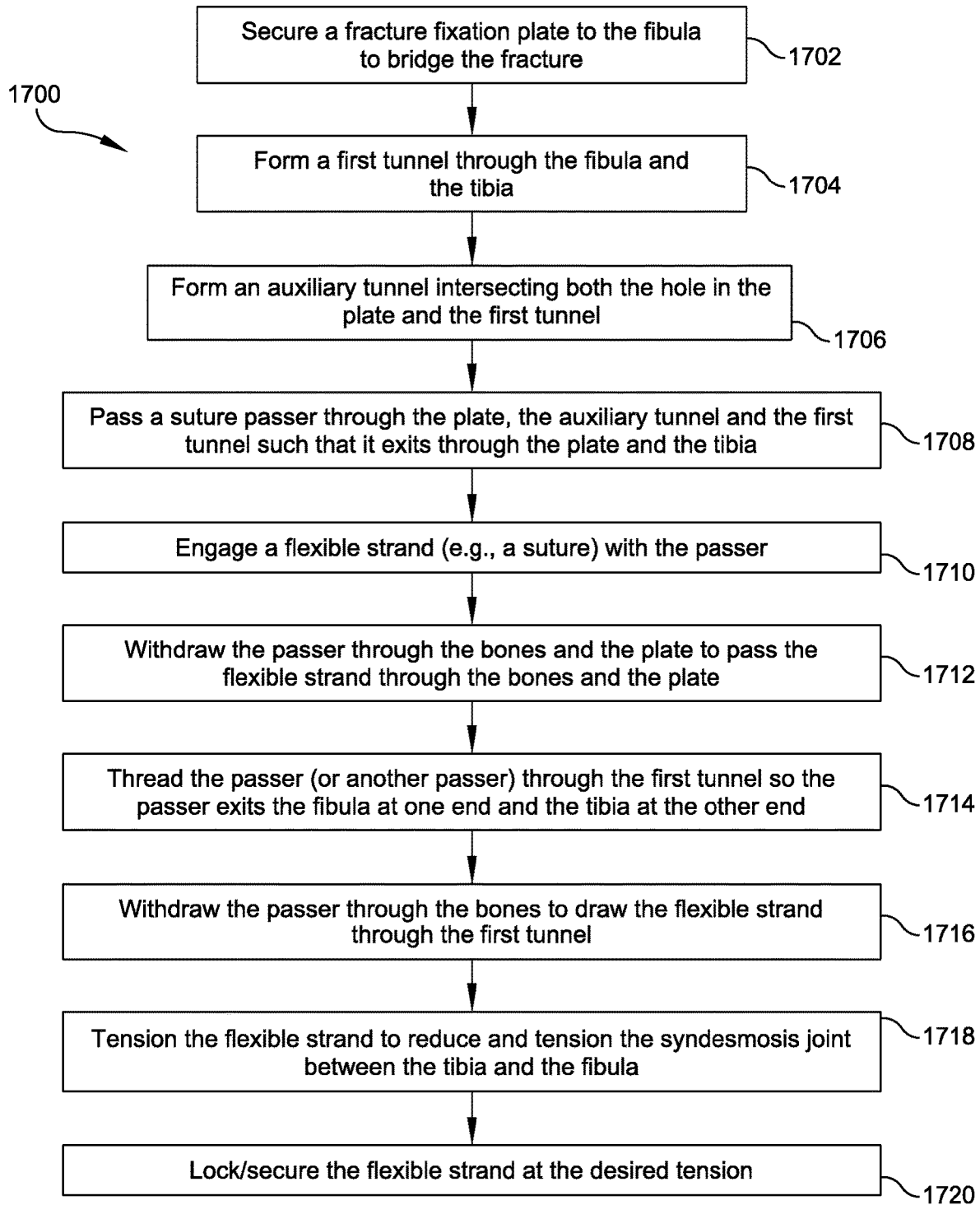
FIG. 49 provides a flowchart detailing the operative sequence illustrated by FIGS. 42-48.

FIGS. 41-47 illustrate the steps of a method 1700 involved in a combined repair of a fibular fracture and a reinforcement of a syndesmosis joint according to exemplary devices and instruments of the invention, while FIG. 49 provides a flowchart depicting the method 1700 detailed in FIGS. 41-52. As background, FIG. 41 illustrates a lateral view of the human ankle 100 illustrating a fracture 116 of the fibular shaft 104.

Figure 42:
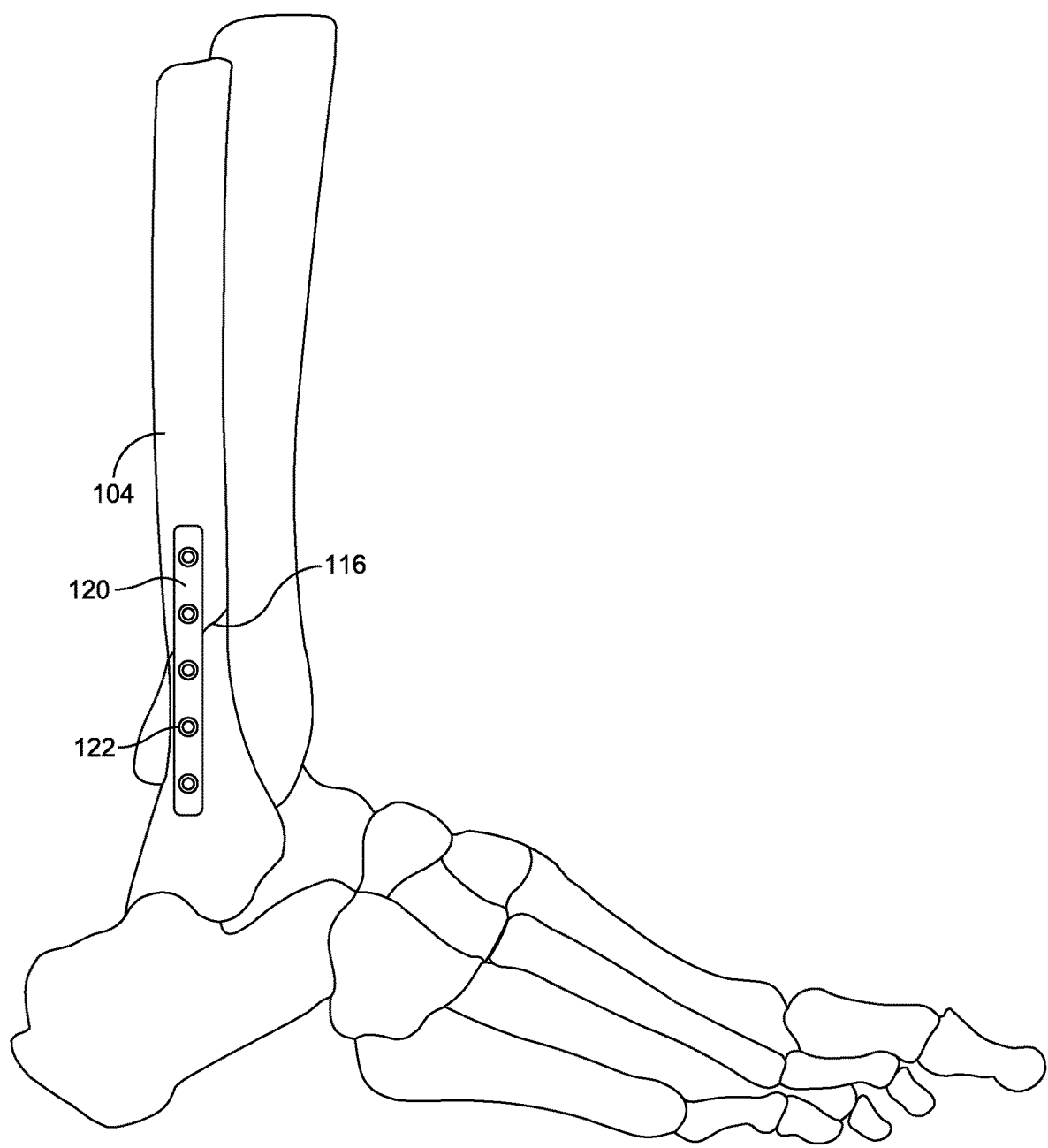
FIG. 42-48 illustrate the steps of an operative sequence for a combined repair of the fibular fracture shown in FIG. 41 and a reinforcement of the syndesmosis joint between the tibia and fibula using embodiments of the disclosed devices.

Referring to FIG. 42, a fracture fixation plate 120, as is known in the art, has been secured to the fibula 104 to bridge the fracture 116 and provide support to the fracture 116 while it heals (FIG. 49, 1702). Such a plate is typically secured by bone screws (not shown) inserted through holes 122 in the plate 120 and extending into the cortical bone on the opposite side of the bone from the plate 120. Embodiments discussed below enable a loop of flexible strand, rather than rigid hardware, to anchor the bone plate 120.

Figure 43:
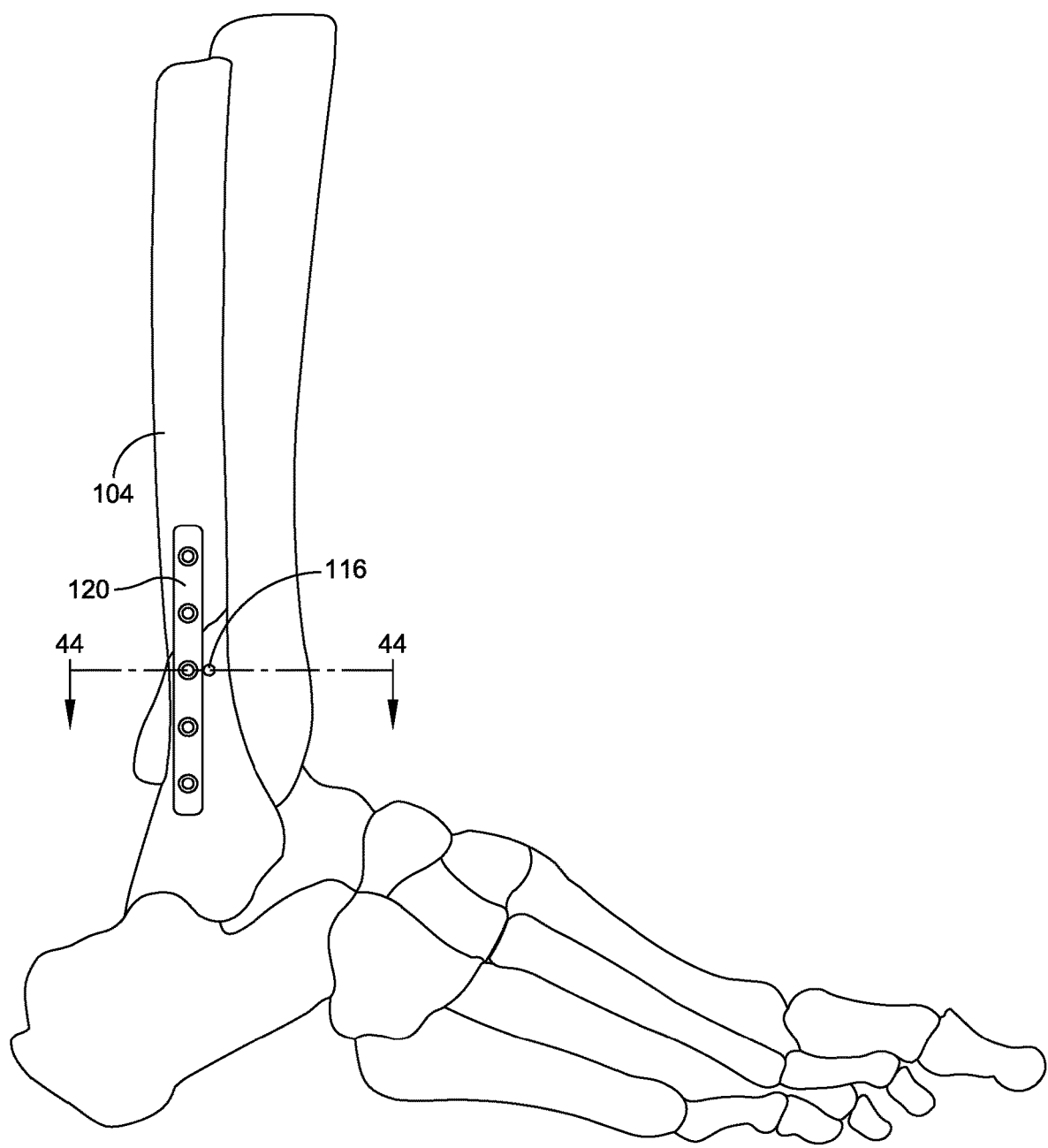
Figure 44:
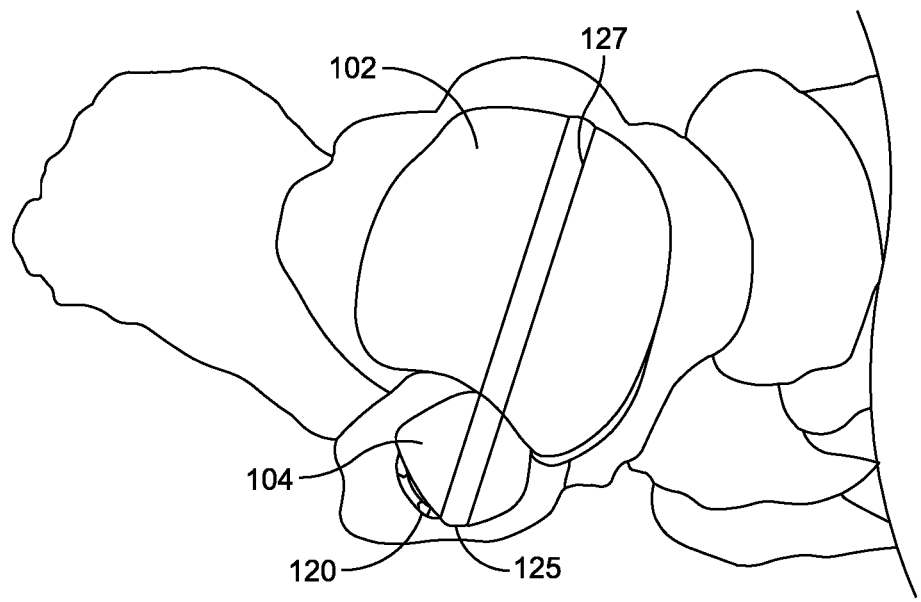

Turning to FIGS. 43-44, a first tunnel 127 has been formed through the fibula 104 and the tibia 102 to accept a stabilization element across the syndesmosis joint to stabilize the joint (FIG. 49, 1704), particularly the interosseous ligament 114. The first tunnel 127 is preferably formed adjacent the edge of the plate 120 and in the same direction as the native ligament to reinforce the ligament during healing. Preferably, the first tunnel 127 passes through the fibular ridge 125 and through the centroid of the fibula 104 and the tibia 102 at the level of fixation. In this embodiment, the first tunnel 127 is formed adjacent to an anterior edge of the plate 120. The first tunnel 127 may be spaced from the plate, more or less, and/or placed on the posterior side of the plate depending on surgeon preference and plate position. In the example of FIGS. 41-52, the plate 120 is positioned posteriorly to accommodate the preferred path for the first tunnel 120 through the bones.

The first tunnel 120 may be formed by drilling, punching, or other suitable tunnel forming means. The first tunnel 120 may be made free hand or with the aid of a guide such as a clamping and drill guide instrument like, for example, the clamp 600 disclosed in FIGS. 6-11 of US patent application Ser. No. 15/642,053, entitled "COMPRESSION AND TENSION INSTRUMENTS AND METHODS OF USE TO REINFORCE LIGAMENTS" 81243.0005) and co-filed with this application on Jul. 5, 2017.

Figure 45:
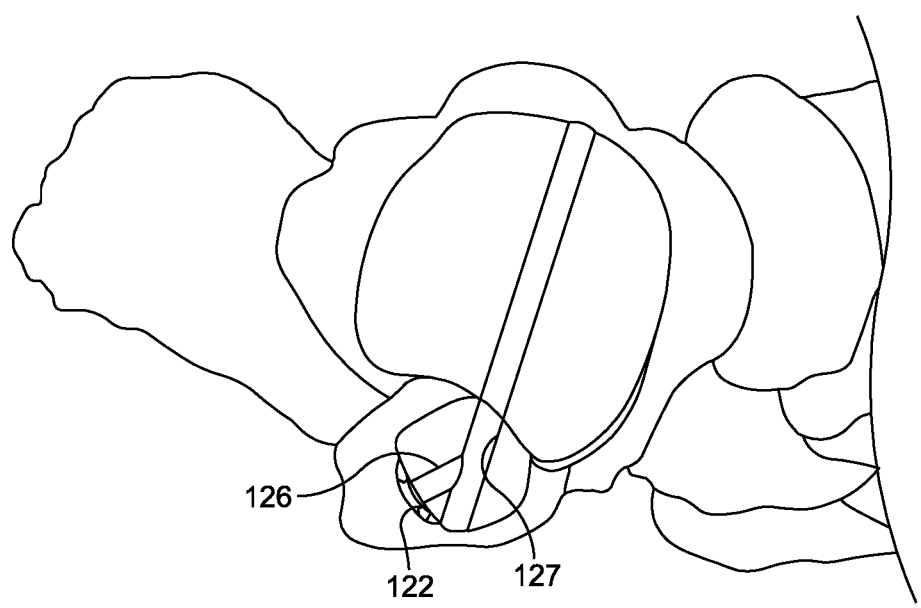

Referring to FIG. 45, an auxiliary tunnel 126 has been formed (FIG. 49, 1706). The auxiliary tunnel 126 intersects both the hole 122 in the plate 120 and the first tunnel 127. The drill may be inserted through a hole within the plate 120 such that the plate itself may serve as a drill guide for the auxiliary tunnel 126.

Figure 46:
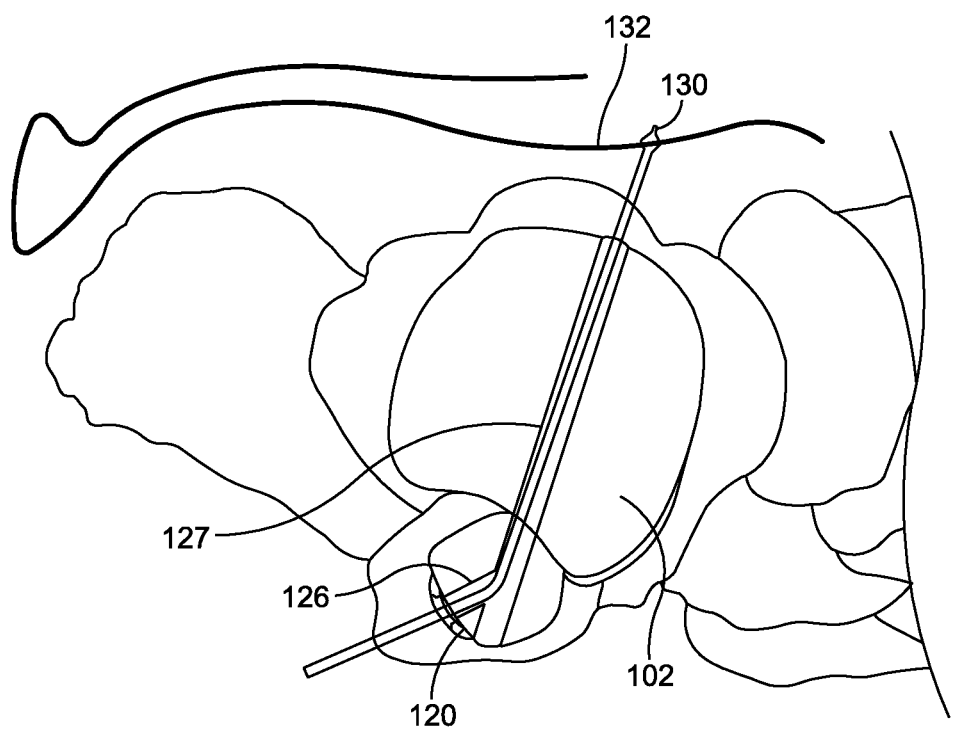

Next, as shown in FIG. 46, a suture passer 130 is passed through the plate 120, the auxiliary tunnel 126, and the first tunnel 127 such that it exits through the plate 120 and the tibia 102 (FIG. 49, 1708). A flexible synthetic strand 132 is then engaged with the passer 130 (FIG. 49, 1710). As discussed above, the flexible synthetic strand may be a high strength suture, suture tape, cable, or another suitable flexible synthetic strand.

Referring to FIG. 47, the passer 130 has been withdrawn through the bones 102, 104 and the plate 120 to pass the flexible strand 132 through the bones and plate 120 (FIG. 49, 1712). The passer 130, or another passer with the flexible strand engaged 132 thereto, is then passed through the first tunnel 120 so it exits the fibula 102 at one end and the tibia 102 at the other end (FIG. 49, 1714).

FIG. 48 illustrates that the passer 130 has been withdrawn through the bones 102, 104 to pass the flexible strand 132 through the first tunnel 127 (FIG. 49, 1716). The flexible strand 132 is now looped around the anterior edge of the plate 120 with two legs of the flexible strand 132 extending across the syndesmosis joint between the tibia 102 and fibula 104. The ends of the flexible strand 132 may now be tensioned to reduce and properly tension the syndesmosis joint (FIG. 49, 1718). The tension may be applied manually by directly pulling on the ends of the flexible strand. Alternatively, a tensioning instrument, such as for example, the tension instrument 700 disclosed in FIGS. 12-15 of US patent application Ser. No. 15/642,053, entitled "COMPRESSION AND TENSION INSTRUMENTS AND METHODS OF USE TO REINFORCE LIGAMENTS" and co-filed with this application on Jul. 5, 2017, may be used to apply and/or indicate the tension. The flexible strand 132 may be secured by, for example, tying the ends over a button anchor, inserting an interference screw into the first tunnel, using one or more staples to secure the ends to the tibial bone surface adjacent the exit hole of the first tunnel 127, or securing the flexible strand with other knotless anchors such as those discussed above in relation to FIGS. 13-29 or disclosed in FIGS. 5-13 of US patent application Ser. No. 15/641,592, entitled "EXTRA JOINT STABILIZATION CONSTRUCT" and co-filed with this application on Jul. 5, 2017, and/or with other suitable means (FIG. 49, 1720).

Figure 50:
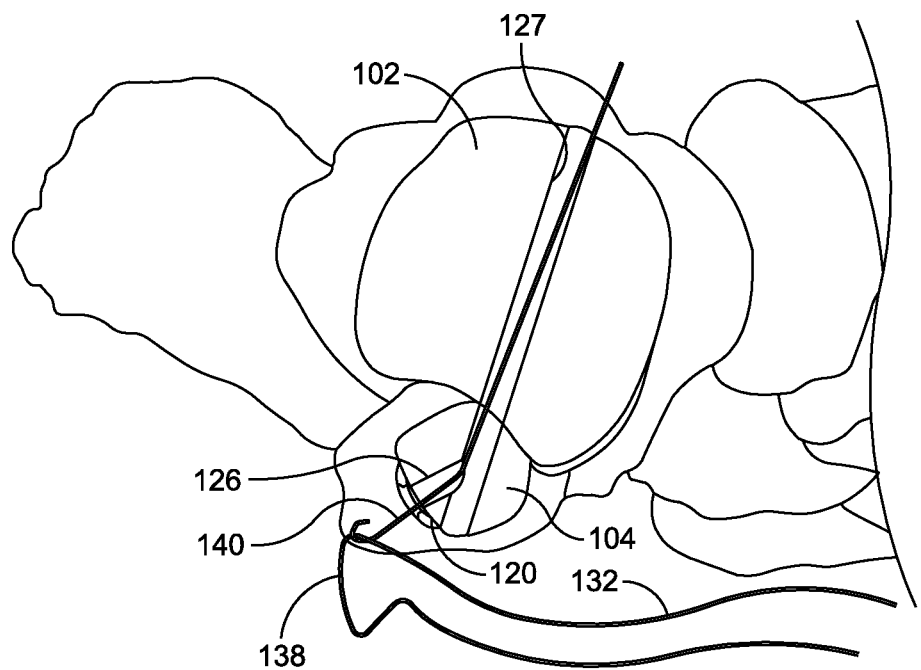
FIGS. 50-53 illustrate alternative steps of an operative sequence for forming a combined repair and reinforcement construct similar to that shown in FIG. 48.
Figure 52:
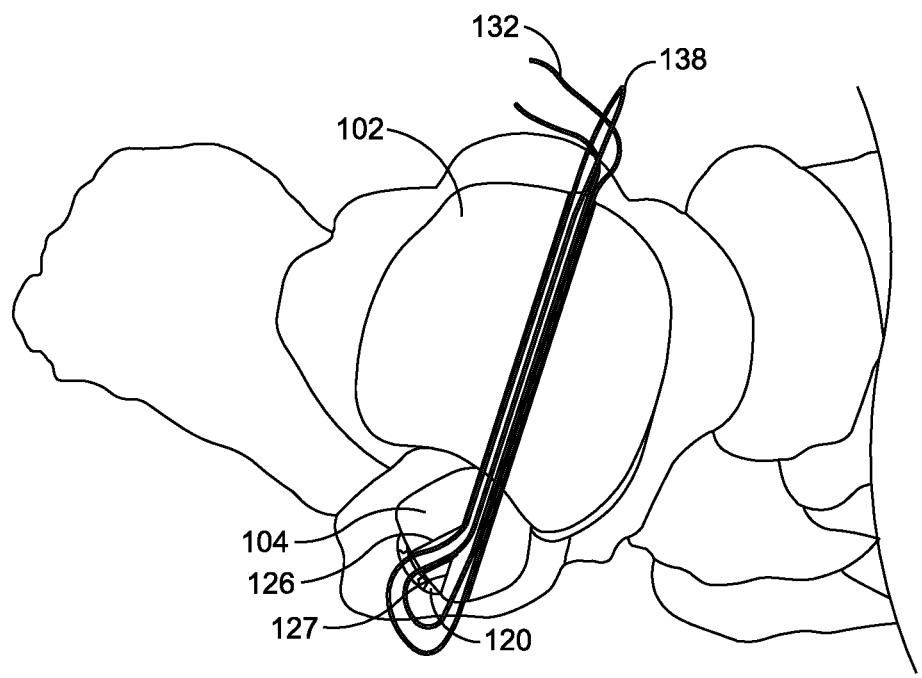
Figure 53:
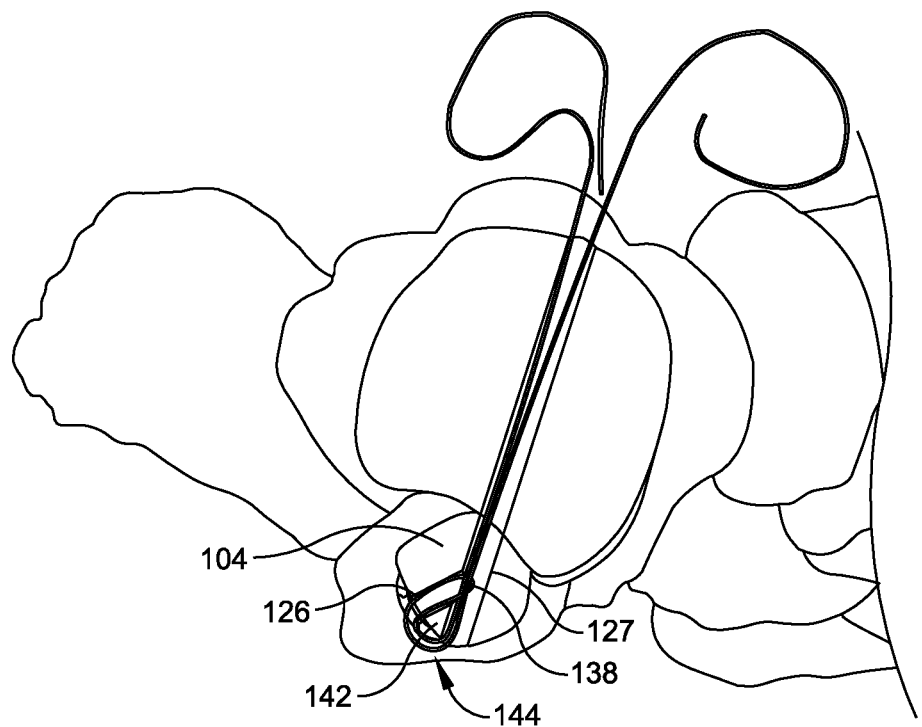
Figure 54:
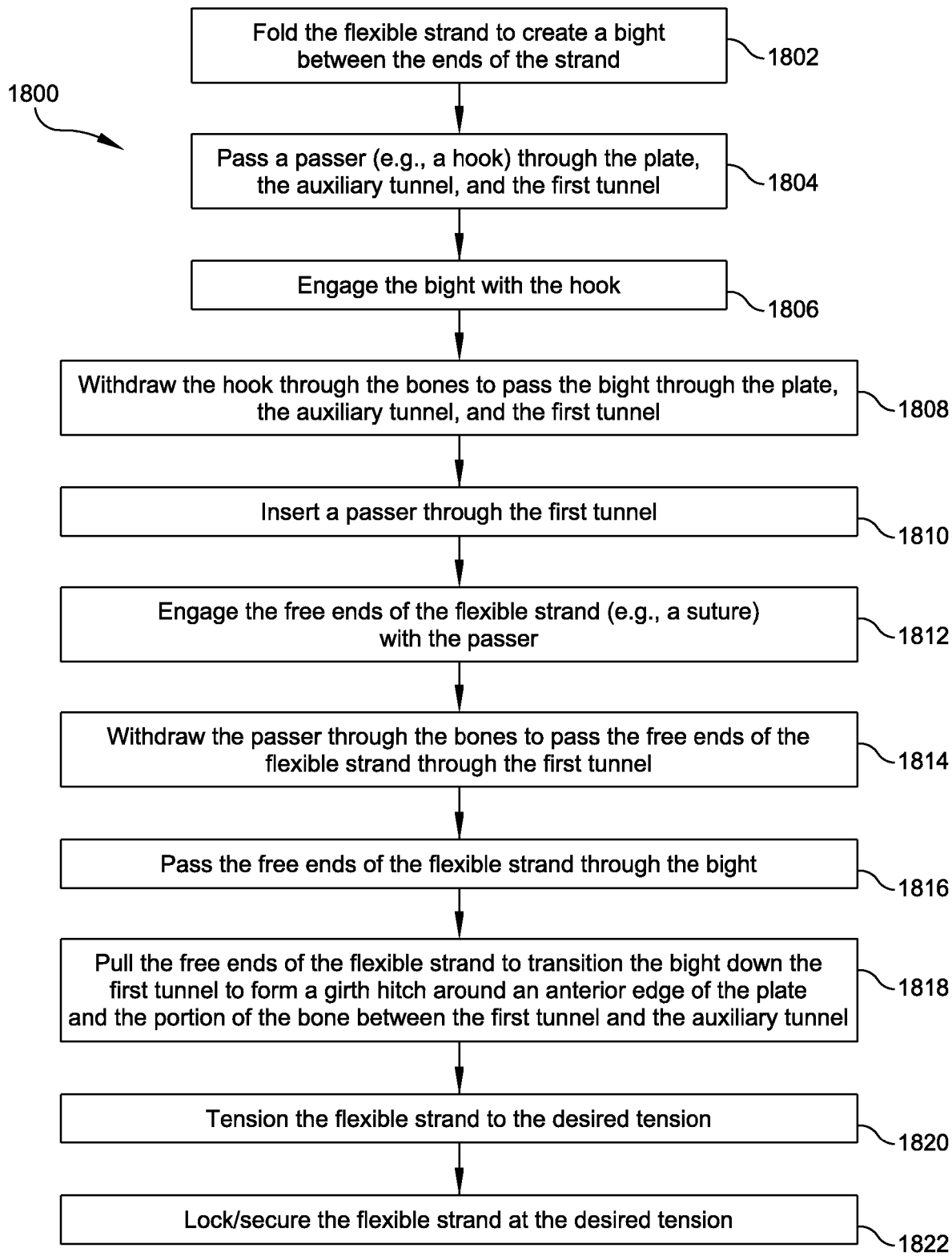
FIG. 54 provides a flowchart detailing the operative sequence illustrated by FIGS. 50-53.

FIGS. 50-53 illustrate alternative steps for passing the flexible strand 130, while FIG. 54 provides a flowchart summarizing a corresponding method 1800. Referring to FIG. 50, the flexible strand 132 is folded to create a bight 138 between the ends of the strand (FIG. 54, 1802), preferably at the approximate center of the strand. A passer such as a hook 140 is passed through the plate 120, the auxiliary tunnel 126, and the first tunnel 127 (FIG. 54, 1804). While the passer 140 may be passed in either direction, it may be simpler to pass it retrograde through the plate 120 first to achieve the position shown in FIG. 50. Once the passer is in position, the bight 138 is engaged with the hook 140 (FIG. 54, 1806).

Figure 51:
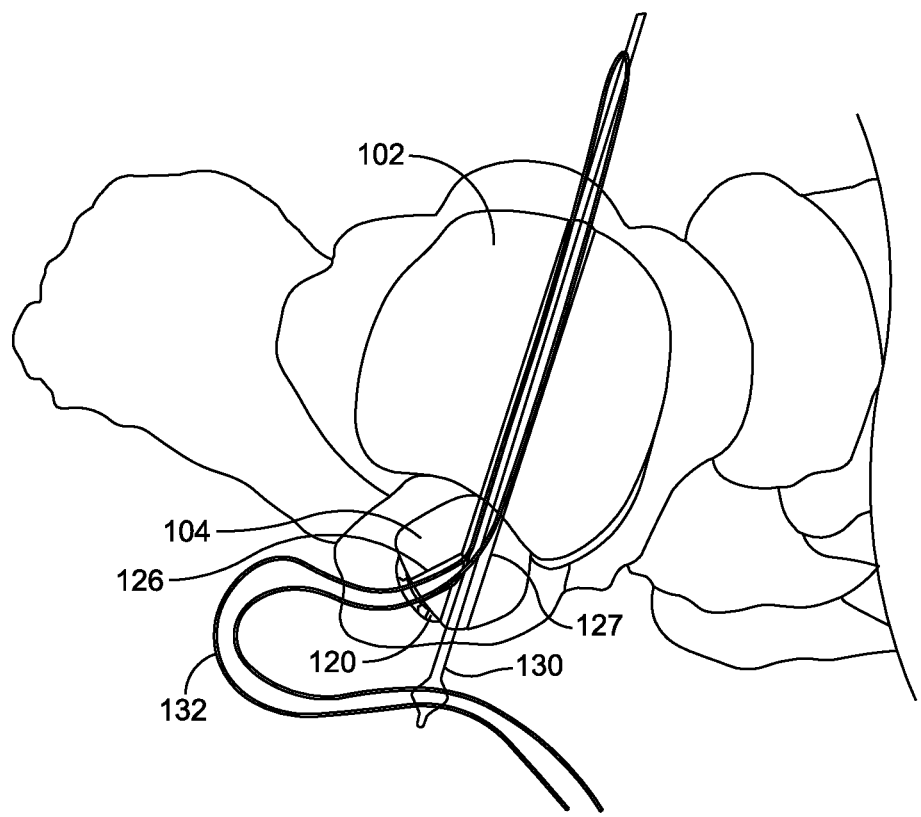

Referring to FIG. 51, the hook 140 has been withdrawn through the bones 102, 104 to pass the bight 138 through the plate 120, the auxiliary tunnel 126, and the first tunnel 127 to exit the tibia 102 (FIG. 54, 1808). A passer, such as passer 130, has been inserted through the first tunnel (FIG. 54, 1810), and the free ends of the flexible strand 132 are engaged with the passer (FIG. 54, 1812).

FIG. 52 illustrates the passer 130 having been withdrawn through the bones to pass the free ends of the flexible strand 132 through the first tunnel 127 (FIG. 54, 1814) before the free ends of the flexible strand 130 have been passed through the bight 138 (FIG. 54, 1816).

Referring to FIG. 53, the free ends of the flexible strand 132 have been pulled to transition the bight 138 down the first tunnel 127 and form a girth hitch 144 around the anterior edge of the plate 120 and the portion of bone 142 between the first tunnel 127 and the auxiliary tunnel 126 (FIG. 54, 1818). If needed, a push rod, forceps, or other device may be used to push on the bight 138 to aid its movement down the tunnel 127 as the free ends are pulled. Forming the girth hitch 144 as shown may improve the direction of the flexible strand 132 through the bones and reduce the tendency of the flexible strand to put pressure on the tunnel edges. The flexible strand 132 may be tensioned (FIG. 54, 1820) and secured (FIG. 54, 1822) as described above in relation to FIG. 48.

The syndesmosis reinforcement sequence according to examples of the invention achieves a very low profile with the flexible strand wrapping the plate edge to secure the bone plate, providing a flexible reinforcement with no rigid hardware spanning the joint. These benefits are accomplished while avoiding radiographic shadowing of the joint interface. Reinforcements according to examples of the invention can accommodate a variety of plate positions, such as more anterior or more posterior since the tunnel can align with, or be offset from, either the anterior or posterior edge of the plate. Reinforcements according to examples of the invention are easily revisable since the flexible strand can simply be cut and the fixation removed from the tibial side of the construct. Notably, the bone plate may be secured upon the fibula, as shown, or the tibia, as desired and/or appropriate.

Although the above embodiments have been described in language that is specific to certain structures, elements, compositions, and methodological steps, it is to be understood that the technology defined in the appended claims is not necessarily limited to the specific structures, elements, compositions and/or steps described. Rather, the specific aspects and steps are described as forms of implementing the claimed technology. Since many embodiments of the technology can be practiced without departing from the spirit and scope of the invention, the invention resides in the claims hereinafter appended.

What is claimed is:

1. A method of at least one of reducing a joint or stabilizing bone, the method comprising:
   forming a first bone tunnel through a first bone;
   forming a second bone tunnel at least partially into a second bone;
   inserting a first anchor with a connected portion of a flexible synthetic strand through the first bone tunnel and into the second bone tunnel such that an end of the flexible synthetic strand extends out of the first bone tunnel;
   routing the end of the flexible synthetic strand through a second anchor comprising an axial hole and a receiver formed in a proximal portion of the second anchor, the receiver having internal threads extending over a proximal portion oriented at a proximal taper angle, a mid portion oriented at a mid taper angle, and a distal portion oriented at a distal taper angle;
   inserting the second anchor into the first bone tunnel;
   tensioning the flexible synthetic strand extending between the first and second anchors; and
   rotationally inserting a set screw into the receiver of the second anchor to lock the flexible synthetic strand relative to the second anchor, the set screw comprising external threads extending over a proximal portion oriented at an opposing proximal taper angle, a mid portion oriented at an opposing mid taper angle, and a distal portion oriented at an opposing distal taper angle, wherein:
   the proximal, the mid, and the distal taper angles of the receiver and the opposing proximal, the opposing mid, and the opposing distal taper angles of the set screw are configured such that the rotationally inserting the set screw into the receiver provides a gradual increase in a proximal compression force applied to the flexible synthetic strand extending between the proximal and the mid portions of the receiver and the set screw and a gradual decrease in a distal compression force applied to the flexible synthetic strand extending between the mid and the distal portions of the receiver and the set screw.

2. The method of claim 1, wherein the first bone and the second bone form a joint therebetween.

3. The method of claim 1, wherein at least one of the first anchor and the second anchor includes a polyaxial washer.

4. The method of claim 1, wherein the locking the flexible synthetic strand relative to the second anchor includes a reversible configuration so as to further allow unlocking the flexible synthetic strand relative to the second anchor.

5. The method of claim 1, wherein:
   the proximal taper angle of the receiver differs from the opposing proximal taper angle of the set screw;
   the mid taper angle of the receiver approximates the opposing mid taper angle of the set screw; and
   the distal taper angle of the receiver differs from the opposing distal taper angle of the set screw.

6. The method of claim 5, wherein the rotationally inserting the set screw into the receiver such that the mid portion of the set screw is positioned distal to a beginning of the mid portion of the receiver and an end of the mid portion of the set screw is positioned proximal to an end of the mid portion of the receiver provides first, second, third, fourth, and fifth zones of clearance between the set screw and the receiver, wherein the first zone provides a maximum proximal clearance between the set screw and the receiver, the third zone provides a minimum clearance between the set screw and the receiver and corresponds with a location at which the mid portions of the set screw and the receiver coincide to apply a maximum compression force to the flexible synthetic strand, and the fifth zone provides a maximum distal clearance between the set screw and the receiver.

7. A method of at least one of reducing a joint or stabilizing bone, the method comprising:
   forming a first bone tunnel through a first bone;
   forming a second bone tunnel through a second bone;
   inserting a first anchor with a connected portion of a flexible synthetic strand into the first bone tunnel and routing the flexible synthetic strand through the first and second bone tunnels such that an end of the flexible synthetic strand extends out of the second bone tunnel;
   routing the end of the flexible synthetic strand through a second anchor having a threaded receiver comprising a proximal portion, a mid portion, and a distal portion;
   inserting the second anchor into the second bone tunnel;
   tensioning the flexible synthetic strand extending between the first and second anchors; and
   locking the flexible synthetic strand relative to the second anchor by rotationally inserting a threaded set screw comprising a proximal portion, a mid portion, and a distal portion, into the threaded receiver, thereby achieving a progressively increasing interference fit about the flexible synthetic strand passing between the proximal portions and the mid portions of the threaded receiver and the threaded set screw and a progressively decreasing interference fit about the flexible synthetic strand passing between the mid portions and the distal portions of the threaded receiver and the threaded set screw.

8. The method of claim 7, wherein the first bone and the second bone form a joint therebetween.

9. The method of claim 7, wherein at least one of the first anchor and the second anchor includes a polyaxial washer.

10. The method of claim 7, further comprising rotationally removing the threaded set screw from the threaded receiver to unlock the flexible synthetic strand relative to the second anchor wherein the locking the flexible synthetic strand relative to the second anchor.

11. The method of claim 7, wherein:
the threaded receiver comprises internal threads extending over the proximal portion oriented at a proximal taper angle, the mid portion oriented at a mid taper angle, and the distal portion oriented at a distal taper angle;
the threaded set screw comprises external threads extending over the proximal portion oriented at an opposing proximal taper angle, the mid portion oriented at an opposing mid taper angle, and the distal portion oriented at an opposing distal taper angle; and
the proximal, the mid, and the distal taper angles of the threaded receiver and the opposing proximal, the opposing mid, and the opposing distal taper angles of the threaded set screw are configured such that the rotationally inserting the threaded set screw into the threaded receiver provides a gradual increase in a proximal compression force applied to the flexible synthetic strand extending between the proximal and the mid portions of the threaded receiver and the threaded set screw and a gradual decrease in a distal compression force applied to the flexible synthetic strand extending between the mid and the distal portions of the threaded receiver and the threaded set screw.

12. The method of claim 11, wherein:
the proximal taper angle of the threaded receiver differs from the opposing proximal taper angle of the threaded set screw;
the mid taper angle of the threaded receiver approximates the opposing mid taper angle of the threaded set screw; and
the distal taper angle of the threaded receiver differs from the opposing distal taper angle of the threaded set screw.

13. The method of claim 12, wherein the rotationally inserting the threaded set screw into the threaded receiver such that the mid portion of the threaded set screw is positioned distal to a beginning of the mid portion of the threaded receiver and an end of the mid portion of the threaded set screw is positioned proximal to an end of the mid portion of the threaded receiver provides first, second, third, fourth, and fifth zones of clearance between the threaded set screw and the threaded receiver, wherein the first zone provides a maximum proximal clearance between the threaded set screw and the threaded receiver, the third zone provides a minimum clearance between the threaded set screw and the threaded receiver and corresponds with a location at which the mid portions of the threaded set screw and the threaded receiver coincide to apply a maximum compression force to the flexible synthetic strand, and the fifth zone provides a maximum distal clearance between the threaded set screw and the threaded receiver.

\* \* \* \* \*